(12) United States Patent
Nakagawa

(10) Patent No.: US 8,926,961 B2
(45) Date of Patent: Jan. 6, 2015

(54) HPV E6 PROTEIN T CELL EPITOPES AND USES THEREOF

(75) Inventor: Mayumi Nakagawa, Little Rock, AR (US)

(73) Assignee: Board Of Trustees of The University Of Arkansas, Little Rock, AR (US)

( * ) Notice: Subject to any disclaimer, the term of this patent is extended or adjusted under 35 U.S.C. 154(b) by 390 days.

(21) Appl. No.: 13/136,557

(22) Filed: Aug. 4, 2011

(65) Prior Publication Data

US 2011/0293651 A1   Dec. 1, 2011

Related U.S. Application Data

(63) Continuation-in-part of application No. 12/286,822, filed on Oct. 2, 2008.

(60) Provisional application No. 60/997,405, filed on Oct. 3, 2007.

(51) Int. Cl.
| | |
|---|---|
| *A61K 39/00* | (2006.01) |
| *A61K 39/12* | (2006.01) |
| *A61K 39/165* | (2006.01) |
| *A01N 63/00* | (2006.01) |
| *C07K 14/005* | (2006.01) |
| *G01N 33/569* | (2006.01) |

(52) U.S. Cl.
CPC ..... *C07K 14/005* (2013.01); *A61K 2039/55511* (2013.01); *A61K 39/00* (2013.01); *G01N 33/56983* (2013.01); *G01N 2333/025* (2013.01); *C12N 2710/20022* (2013.01)
USPC ............... 424/93.5; 424/93.51; 424/186.1; 424/204.1; 424/212.1; 424/274.1; 424/278.1

(58) Field of Classification Search
None
See application file for complete search history.

(56) References Cited

U.S. PATENT DOCUMENTS

2006/0182763 A1*   8/2006   Kim et al. ............... 424/204.1

FOREIGN PATENT DOCUMENTS

| WO | WO9322338 A1 | * 11/1993 |
|---|---|---|
| WO | WO 2004/105681 | * 12/2004 |

OTHER PUBLICATIONS

Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
Fradet-Turcotte and Archambault (Antiviral Therapy, 2007, 12: 431-451).*
A_GENSEQ AAR43777.*
Gen Bank AAD33252.1, Flores et al. 2000.*

* cited by examiner

*Primary Examiner* — Gerald R Ewoldt
*Assistant Examiner* — Marianne DiBrino
(74) *Attorney, Agent, or Firm* — Hugh McTavish

(57) ABSTRACT

The present invention is directed to the examination of the pattern of immunodominant T cell epitopes in the E6 protein of Human Papilloma virus and its further characterization in terms of its amino acid sequence and Human Leukocyte Antigen restriction. These epitopes are identified based on their ability to induce specific T cell responses and therefore, are important as sources of antigens for immunotherapies to treat cervical and other cancers. The present invention contemplates identifying a number of similar epitopes restricted by a wide variety of Human Leukocyte Antigen types so that they can be used together to develop preventative or therapeutic vaccines, which can be used for the general human population. The present invention also contemplates using E6 peptides of Human Papilloma virus as a diagnosis method to predict the probability of developing persistent cervical neoplasia in an individual.

20 Claims, 14 Drawing Sheets

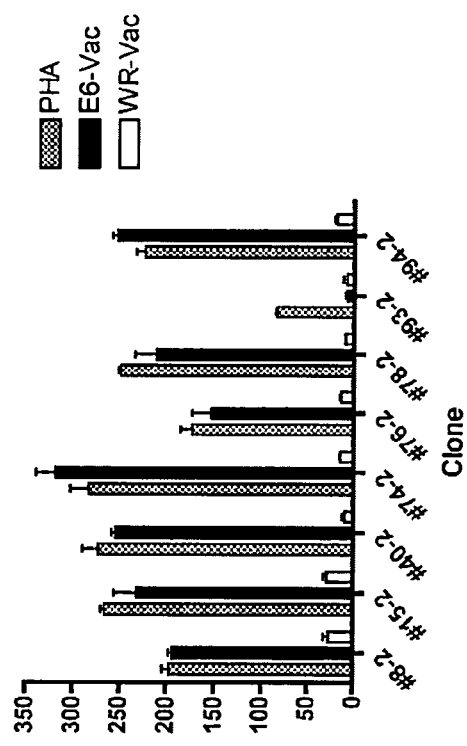
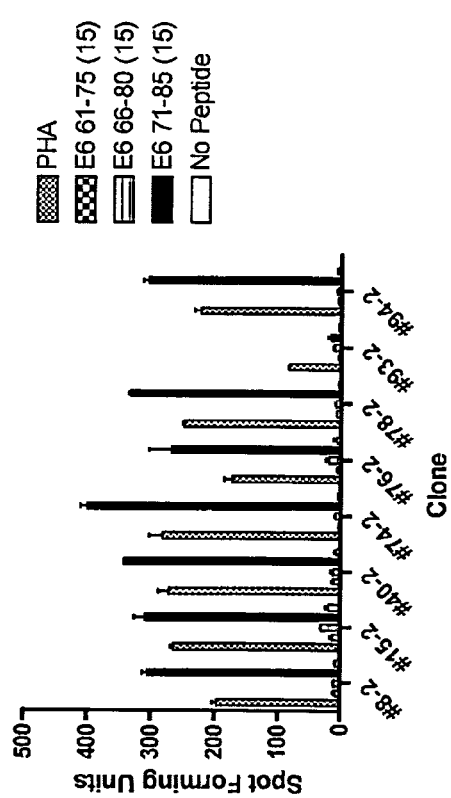
FIG. 2B
FIG. 2A

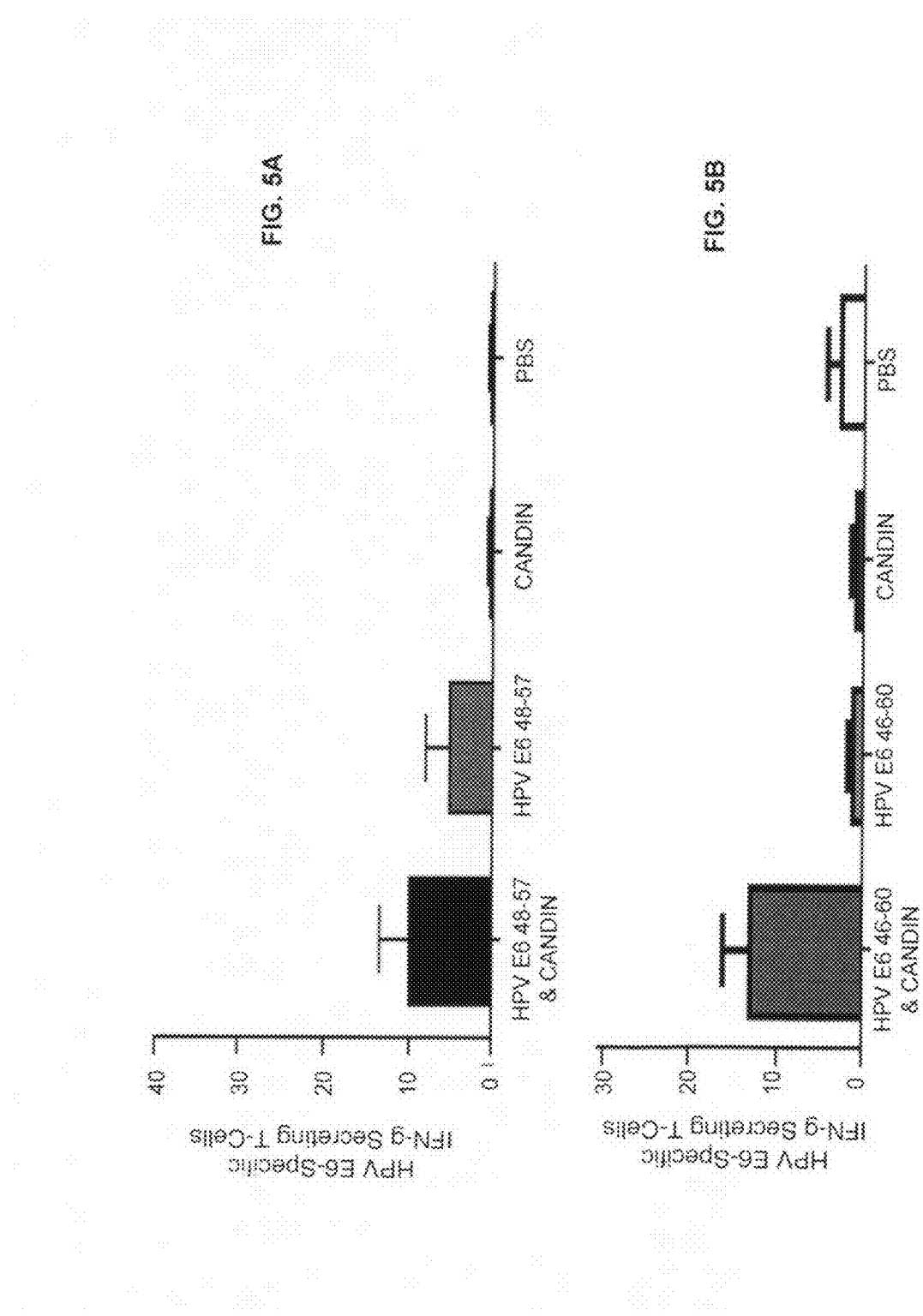

HPV E6 PROTEIN T CELL EPITOPES AND USES THEREOF

CROSS-REFERENCE TO RELATED APPLICATION

This continuation-in-part application claims benefit of priority under 35 U.S.C. §120 of pending non-provisional application U.S. Ser. No. 12/286,822, filed on Oct. 2, 2008, which claims benefit of priority under 35 U.S.C. §119(e) of provisional application U.S. Ser. No. 60/997,405 filed on Oct. 3, 2007, the entirety of both of which are herein incorporated by references.

FEDERAL FUNDING LEGEND

This invention was made with government under grant number CA051323 awarded by the National Institutes of Health. The government has certain rights in this invention.

BACKGROUND OF THE INVENTION

1. Field of the Invention

The present invention relates generally to the field of immunology. More specifically, the present invention involves identification of dominant CD8 T cell epitopes in the Human Papilloma virus (HPV) proteins and its use in treating cancer such as cervical cancer.

2. Description of the Related Art

Cervical cancer is the second most common malignancy among women worldwide (1) with 400,000 new cases annually (2). Annually 12,000 to 14,000 new cases of squamous cell cancer of the cervix are reported in the United States (3), resulting in about 3,500 deaths per year. High-risk Human Papilloma virus, the most commonly HPV16, is the major cause of cervical cancer (4-5). Among the over one hundred different types of Human Papilloma virus, at least 15 are strongly associated with invasive squamous cell cancer of the cervix (6). HPV16 is the one most commonly found associated with this cancer (7-8).

Human Papilloma virus infection is also associated with the precursor lesion of cervical cancer, squamous intraepithelial lesion (7-12). While most low-grade squamous intraepithelial lesions prospectively regress spontaneously (13-14), some progress to high-grade squamous intraepithelial lesions. These high-grade lesions, in particular, cervical intraepithelial neoplasia-3 is associated with a high rate progression to invasive cervical cancer (15-16).

Two early gene products, E6 and E7, mediate transformation to a malignant phenotype by Human Papilloma virus. Both of these viral proteins have been shown to interact with the products of cellular human tumor suppressor genes. The E6 protein can bind and promote degradation of cell-encoded p53, while the E7 protein interacts with the retinoblastoma susceptibility gene product. Constitutive expression of HPV E6/E7 proteins is required for the maintenance of a malignant phenotype of cervical cancer (5, 17). Moreover, HPV16 E6 and E7 proteins contain many antigenic epitopes and are foreign viral antigens. These proteins may, therefore, represent targets of antigen-specific immunotherapeutic strategies for the prevention and treatment of cervical cancer.

Cell-mediated immunity plays an important role in controlling Human Papilloma virus infection and Human Papilloma virus-associated diseases. CD4 T cells are important in the development of anti-tumor responses (18-21). It is believed that the effectiveness of these CD4 T cells lies in their ability to deliver help for priming and maintaining CD8 cytotoxic T lymphocytes, which are thought to serve as the dominant effector cells in tumor elimination. Immunohistochemical analyses of squamous intraepithelial lesions and cervical cancer specimens have demonstrated the presence of activated cytotoxic T lymphocytes in lesions (22). The CD4 T cells activate cytotoxic T lymphocytes by producing T helper 1 cytokines (23) and by providing activation signals for priming of tumor-specific cytotoxic T lymphocytes to professional antigen presenting cells (24-27). CD8-positive cytotoxic T lymphocytes recognize foreign peptides that are 8 to 11 amino acids in length and bound to and presented by Human Leukocyte Antigen class I molecules. These peptides are called T cell epitopes.

A study identified epitopes of HPV16 E6 and E7 proteins by using overlapping peptides of these proteins to stimulate peripheral blood mononuclear cells from a healthy donor and binding assays to find candidate epitopes (28). This approach enabled the identification of Human Leukocyte Antigen-B18 epitopes, E6 80-88 (ISEYRHYCY; SEQ ID NO: 24) and E7 44-52 (QAEPDRAHY: SEQ ID NO: 28). It was also shown that E6 80-88 was a naturally processed epitope that could be recognized by T cells from a patient with high-grade squamous intraepithelial lesion. Although the binding of the peptide to the Human Leukocyte Antigen molecule was demonstrated, the strength of the T cell response to these antigenic epitopes compared with other T cell epitopes was not assessed, and it was not clear whether this peptide had a protective effect.

A study using stimulated peripheral blood mononuclear cells from cervical cancer patients with an Human Leukocyte Antigen-A2-restricted HPV16 E7 peptide (E7 11-20) showed that cytotoxic T lymphocytes were capable of lysing Human Leukocyte Antigen-matched HPV16 E7 11-20-pulsed targets in two of three patients (29). Further, another group identified HPV-specific cytotoxic T lymphocytes in lymph nodes and tumors of cervical cancer patients (30). In previous work examining cytotoxic T lymphocyte responses to HPV16 in HPV16-infected women (no squamous intraepithelial lesion), cytotoxic T lymphocyte responses to the HPV16 E6 protein, but not to the E7 protein, were significantly associated with the clearance of HPV16 infection (31).

These observations have demonstrated HPV16 E6- and/or E7-specific cytotoxic T lymphocytes in women with and without squamous intraepithelial lesion and in women with cervical cancer. Efforts have been made to define the viral epitopes inducing the Human Papilloma virus-specific cytotoxic T lymphocyte that are responsible for the clearance of virus-infected and virus-transformed cells. Using the same approach as was taken for HPV16, Human Leukocyte Antigen-A2.1 binding synthetic peptides of HPV18 E6 protein were identified (32). Some of these binding peptides were also shown to be antigenic by demonstrating in vitro cytotoxicity.

High-risk human Papilloma virus peptide antigens for CD8 T lymphocytes have been shown to be antigenic in human experimental systems by demonstrating peptide-specific cytotoxicity or interferon-γ secretion. Except for the Human Leukocyte Antigen-B18-restricted epitopes identified by Bourgault Villada et al., all were pre-selected for the given Human Leukocyte Antigen types. None of the antigenic epitopes were identified based on the magnitude of T cell response regardless of the restricting Human Leukocyte Antigen molecules.

Memory T cells play an important role in maintaining long-term immunity to previously encountered pathogens or tumor antigens. They may proliferate, and rapidly acquire effector functions to kill virus-infected cells or tumor cells, and secrete cytokines that inhibit replication of the pathogen after re-stimulation with re-exposure to antigen (33). Antigen presenting cells, which may transfer peripheral antigenic signals to the lymphoid organs, play a crucial role in the induction of antigen-specific T cell immunity responses to Human Papilloma virus infection and Human Papilloma virus-associated tumors. Dendritic cells as professional antigen presenting cells express high level of major histocompatibility complex and co-stimulatory molecules. Insufficient or improper activation of dendritic cells, caused by lack of pro-inflammatory signal, leading to antigen presentation not in an appropriate co-stimulatory context is one reason for the failure of antitumor immunity. Vaccination with autologous, tumor antigen loaded properly activated dendritic cells in vitro present promising immunotherapy modality for tumors. With the development of techniques for dendritic cell isolation, antigen loading and maturation, dendritic cell-based vaccines has progressed in recent decade (34-35).

Thus, the prior art is deficient in peptide antigens, derived from the Human Papilloma virus E6 protein useful as vaccine antigens or for dendritic cell immunotherapy to treat cervical cancers. The present invention fulfills this long-standing need and desire in the art.

SUMMARY OF THE INVENTION

In one embodiment of the present invention, there is provided a method of determining immunodominant T cell epitopes within a protein in an individual. This method comprises pulsing dendritic cells obtained from the individual with a recombinant protein and establishing T cell lines by stimulating peripheral blood mononuclear cells (PBMCs) with the dendritic cells. The T cell lines thus established are then incubated with peptides representative of the protein and the specific T cell response in the incubated cells is then measured. Subsequently, peptides that induce T cell response are identified, where the sequence of the peptide corresponds to a region within the protein, thereby determining the immunodominant T cell epitopes within the protein in the individual. The peptides that induce a T cell response are identified, wherein the sequence of the peptides corresponds to a region within the Human Papilloma virus protein. Thus, the pattern of the immunodominant T cell epitopes within the Human Papilloma virus protein is determined.

In another related embodiment of the present invention, there is provided a method of immunotherapy targeted towards a protein in an individual. This method comprises isolating immune cells from the individual and incubating the isolated immune cells with peptides comprising one or more of the immunodominant T cell epitopes identified using the method described supra. These immune cells are then transferred back to the individual such that the transferred immune cells produce a specific immune response in the individual, thereby generating immunotherapy targeted towards the protein in the individual.

In yet another related embodiment of the present invention, there are provided synthetic peptides selected from the group consisting of SEQ ID NO. 1, SEQ ID NO. 2, SEQ ID NO. 3, SEQ ID NO. 4; SEQ ID NO. 5; SEQ ID NO. 6; SEQ ID NO. 7, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or SEQ ID NO: 37.

In still another related embodiment of the present invention, there is provided an immunogenic composition comprising one or more of the synthetic peptides identified supra.

In yet another embodiment of the present invention, there is provided a method of preventing or treating a pathophysiological condition involving expression of protein in an individual. Such a method comprises administering an immunologically effective amount of the immunogenic composition identified herein, where the composition activates a specific immune response in the individual, thereby preventing or treating the pathophysiological condition in the individual.

In yet another embodiment of the present invention, there is provided a method for increasing regression of human papilloma virus (HPV)-associated cervical lesions in an HPV positive individual. Such a method comprises administering an immunogenic composition comprising two or more peptides derived from two or more immunodominant epitopes of HPV E6 or E7 protein effective to generate CD8 T-cell responses specific against the HPV.

In yet another embodiment of the present invention, there is provided a method to predict the probability of developing persistent cervical neoplasia in an individual, consisting the steps of: 1) obtaining whole blood from the individual; 2) establishing mature dendritic cells by pulsing the dendritic cells from the whole blood with a peptide fragment of an E6 protein of a Human Papilloma Virus; 3) establishing a T cell line by combining T cells from the whole blood with the mature dendritic cells; 4) determining the percentage of T cells in the T cell line that respond to the peptide fragment of an E6 protein of a Human Papilloma Virus. In such a method, a higher T cell response to the peptide fragment from the individual being diagnosed than a T cell response to the same peptide fragment from an individual without cervical neoplasia indicates that the individual with higher T cell response is more likely to develop persistent cervical neoplasia.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIG. 1A shows for subject 2, the Human Papilloma virus infection was detected at one visit, the T cell clones isolated to define the dominant CD8 T cell epitope are derived from a blood sample drawn 53 months after Human Papilloma virus clearance. FIG. 1B shows subject 18, whose HPV16 infection persisted for about 4 years. Peripheral blood mononuclear cells for the cultured enzyme-linked immunospot assay were isolated from blood sample collected 4, 22, 27, 48 and 74 months after the clearance of this infection. The T cell clones isolated to define the dominant CD8 T cell epitope derived from a blood sample drawn 78 months after Human Papilloma virus clearance.

FIGS. 2A-2F show the characterization of subject 2's dominant CD8 T cell epitope in terms of its minimal and optimal amino acid sequence and the Human Leukocyte Antigen restricting molecule. The bars represent standard errors of the means. FIG. 2A shows an enzyme-linked immunospot assay performed to retest the screen-positive T cell clones. Three 15-mer peptides contained in the positive pool were tested individually in duplicate or triplicate. Seven of eight positive T cell clones demonstrated positive responses with the E6 71-85 peptide, but not with E6 61-75 and E6 66-80 peptides. FIG. 2B shows an enzyme-linked immunospot assay was performed using the screen-positive T cell clones, with vaccinia virus expressing E6 protein (E6-vac) or wild type vaccinia virus, Western Reserve (WR-vac), at a multiplicity of infection of 5. Seven of eight screen-positive T cell clones demonstrated a strong positive response with vaccinia virus expressing E6 protein infected autologous Epstein-Barr Virus-transformed B-lymphoblastoid cell line cells, but not with wild type vaccinia virus infected autologous Epstein-Barr Virus-transformed B-lymphoblastoid cell line cells. FIG. 2C shows an enzyme-linked immunospot assay performed using the T cell clones, with 9-mer peptides overlapping by 8 amino acids, contained within the screen-positive 15-mer peptide. Seven T cell clones demonstrated a strong positive response with the SEQ ID NO. 1 E6 75-83 peptide, followed by the E6 74-82 peptide. FIG. 2D shows an enzyme-linked immunospot assay performed using the T cell clones, with two 10-mer peptides surrounding SEQ ID NO. 1 E6 75-83 and two 8-mer peptides within it. The results were equally strong with the SEQ ID NO. 1 E6 75-83 9-mer and the E6 74-83 10-mer. FIG. 2E shows a comparison of the SEQ ID NO. 1 E6 75-83 9-mer peptide and the E6 74-83 10-mer peptide, ranging from $10^{-5}$M to $10^{-10}$M, demonstrating that the optimal peptide of minimum length is the SEQ ID NO. 1 E6 75-83 9-mer. FIG. 2F shows a chromium release assay was performed using peptides-pulsed autologous or a panel of partially Human Leukocyte Antigen-matched autologous Epstein-Barr Virus-transformed B-lymphoblastoid cell line cells as antigen presenting cells. Human Leukocyte Antigen-B62 was demonstrated to be the restricting molecule for the CD8 epitope of SEQ ID NO. 1 E6 75-83. A representative (#78-2) of the two clones was shown. E:T ratio, effector-to-target T cell ratio. θ, autologous Epstein-Barr Virus-transformed B-lymphoblastoid cell line cells. *, Human Leukocyte Antigen type determined using one of the molecular methods.

FIG. 3A shows an enzyme-linked immunospot assay performed using eight screen-positive T cell clones, with the three 15-mer peptides contained in the HPV16 E6 121-145 region. All T cell clones demonstrated positive responses with the E6 131-145 peptide, but not with the E6 121-135 and E6 126-140 peptides. FIG. 3B shows an enzyme-linked immunospot assay was performed using eight screen-positive T cell clones, with vaccinia virus expressing E6 protein, vaccinia virus expressing E7 protein or Western Reserve wild type vaccinia virus at multiplicity of infection of 5. All eight tested T cell clones demonstrated a strong positive response with vaccinia virus expressing E6 protein, yet not with vaccinia virus expressing E7 protein and wild type vaccinia virus. FIG. 3C shows an enzyme-linked immunospot assay was performed using two T cell clones, with 10-mer peptides overlapping by 9 amino acids contained within the screen-positive 15-mer peptide. Both T cell clones demonstrated a strong positive response with the SEQ ID NO. 2 E6 133-142 peptide, but not with other 10-mer peptides. FIG. 3D shows an enzyme-linked immunospot assay was performed using four T cell clones, with different length of peptides surrounding the SEQ ID NO. 2 E6 133-142 10-mer peptide. The two 11-mer peptides surrounding this SEQ ID NO. 2 E6 133-142 10-mer peptides and the 10-mer were positive but not the 9-mer peptides within the 10-mer. FIG. 3E shows a comparison of the SEQ ID NO. 2 E6 133-142 10-mer peptide, the E6 132-142 11-mer peptide, and the E6 133-143 11-mer peptide ranging from $10^{-5}$M to $10^{-10}$M, demonstrating that the optimal peptide of minimum length is the SEQ ID NO. 2 E6 133-142 10-mer. FIG. 3F shows a chromium release assay was performed using peptide-pulsed autologous or a panel of partially Human Leukocyte Antigen-matched autologous Epstein-Barr Virus-transformed B-lymphoblastoid cell line cells as the antigen presenting cells. The Human Leukocyte Antigen-A6801 molecule but not the Human Leukocyte Antigen-A6802 molecule appears to be the restricting molecule for the CD8 epitope of SEQ ID NO. 2 E6 133-142. A representative (#1-18) of the two clones was shown. E:T ratio, effector-to-target T cell ratio. θ, autologous Epstein-Barr Virus-transformed B-lymphoblastoid cell line cells. *, Human Leukocyte Antigen type determined using one of the molecular methods. The bars represent standard errors of the means.

FIGS. 5A-5C show intracellular cytokine staining of spleen cells from vaccinated C57BL/6 mice. A higher numbers of T-cells specific for HPV E6 were detected in mice vaccinated with HPV E6 peptides with CANDIN (Allermed, San Diego, Calif.) as adjuvant, compared to the number of specific T cells from mice vaccinated with either the antigen or the adjutant alone. FIG. 5A shows the results obtained using HPV 16 E6 48-57 (SEQ ID No: 36, 10-mer, EVYD-FAFRDL) as antigen. FIG. 5B shows the results obtained using HPV 16 E6 46-60 (SEQ ID No: 37, 15-mer, RREVY-DFAFRDLCIV) as antigen. FIG. 5C shows the results obtained using HPV 16 E6 46-80 (SEQ ID No: 33, 35-mer, $CH_3$—$NH_2$) as antigen. SEQ ID No: 33 is acetylated ($CH_3$—) at the amino terminus and amidated at the carboxyl ternius (—$NH_2$) to enhance stability. The results from one of the two experiments in which mice were injected thrice every two weeks are shown.

DETAILED DESCRIPTION OF THE INVENTION

As used herein, the term, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Some embodiments of the invention may consist of or consist essentially of one or more elements, method steps, and/or methods of the invention. It is contemplated that any method or composition described herein can be implemented with respect to any other method or composition described herein.

ecules; SEQ ID NO. 5 (E6 127-142) restricted by HLA-A68 and -DR1 molecules; SEQ ID NO. 6 (E6 11-38) restricted by HLA-A2.1, -B48 and -B61 molecules; SEQ ID NO. 7 (E6 49-88) restricted by HLA-A24, -B18, -B35, -B57 and -B62 molecules (Table 1).

TABLE 1

Human Papilloma virus HPV16 E6-specific dominant T cell epitopes and peptide regions of multiple T cell epitopes

| Sequence Identification (SEQ ID NO.) | HPV16 E6 Peptide Region | Peptide Amino Acid Sequence | Human Leukocyte Antigen Restriction Element |
|---|---|---|---|
| 1 | HPV16 E6 75-83 | KFYSKISEY | HLA-B62 |
| 2 | HPV16 E6 133-142 | HNIRGRWTGR | HLA-A68 |
| 3 | HPV16 E6 49-61 | VYDFAFRDLCIVY | HLA-A24, -B35, and -B57 |
| 4 | HPV E6 75-88 | KFYSKISEYRHYCY | HLA-B18 and -B62 |
| 5 | HPV16 E6 127-142 | DKKQRFHNIRGRWTGR | HLA-A68 and -DR1 |
| 6 | HPV16 E6 11-38 | DPQERPRKLPQLCTELQTTIHDIILECV | HLA-A2.1, -B48 and -B61 |
| 7 | HPV16 E6 49-88 | VYDFAFRDLCIVYRDGNPYAVCDKCLKFYSKISEYRHYCY | HLA-A24, -B18, -B35, -B57 and -B62 |

As used herein, the term "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

Figure 1A:
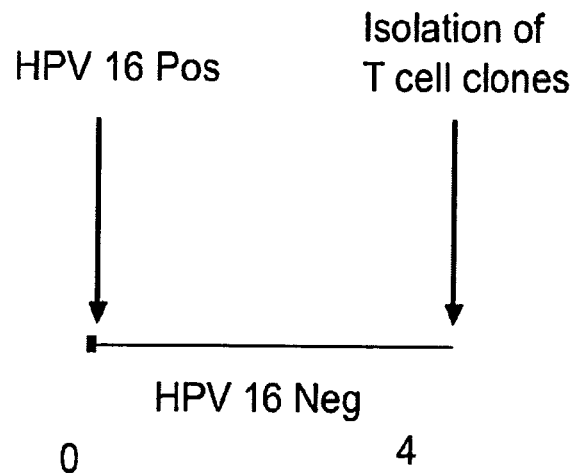
FIGS. 1A-1B show the natural history of HPV16 infection.
Figure 1B:
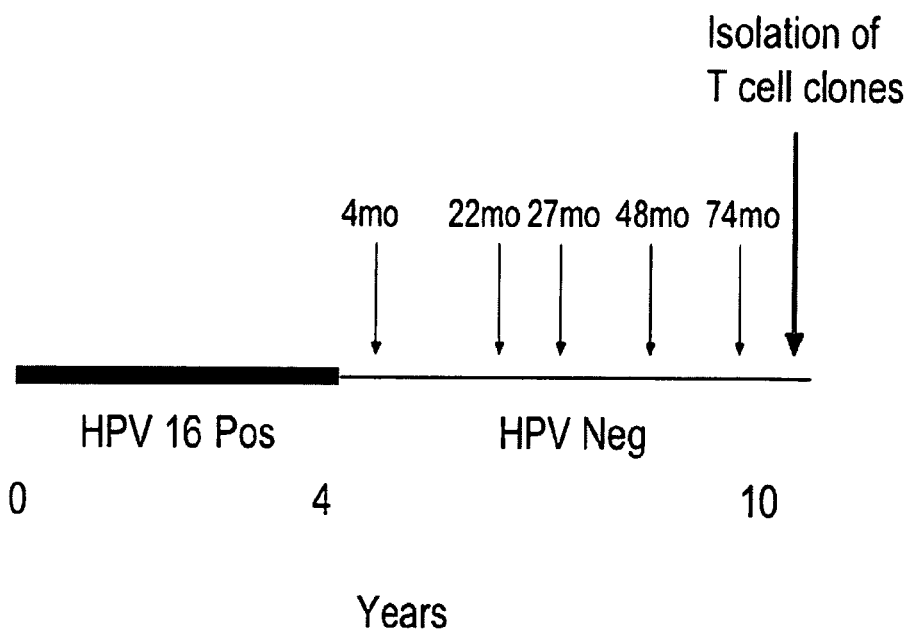

The present invention examined the pattern of Human Papilloma virus-specific CD8 T cell epitopes in the HPV16 E6 protein recognized by T lymphocytes from women demonstrating evidence of HPV-16 clearance (i.e., at least two consecutive HPV-16-negative tests after an initial HPV-16-positive test). The female subjects were participants of a longitudinal study of Human Papilloma virus infection, and were monitored using cervical Human Papilloma virus DNA testing by PCR (36), cytology, and colposcopy every 4 months. Subject 2's HPV16 infection was detected at a single visit and the blood to establish the CD8 T cell line was drawn 53 months later. Subject 18 had an HPV16 infection lasting more than 4 years, and the blood sample was taken 53 months after clearance (FIGS. 1A-1B). CD8 T cell lines, obtained from blood samples drawn after Human Papilloma virus infection clearance, were established by in vitro stimulation of CD8 T cells with autologous dendritic cells infected with vaccinia virus expressing the Human Papilloma virus E6 recombinant protein.

An object of the present invention is to further define for Human Papilloma virus HPV16 E6 protein the minimal and optimal amino acid sequences and the corresponding Human Leukocyte Antigen restricting molecules of the dominant CD8 T cell epitopes within those regions. Two novel HPV16 E6 CD8 T cell epitopes, SEQ ID NO. 1 E6 75-83 (KFYSKISEY) restricted by HLA-B62 and SEQ ID NO. 2 E6 133-142 (HNIRGRWTGR) restricted by HLA-A68, were determined. Additional regions which contain multiple T cell epitopes were identified as follows: SEQ ID NO. 3 (E6 49-61) restricted by HLA-A24, -B35, and -B57 molecules; SEQ ID NO. 4 (E6 75-88) restricted by HLA-B18 and -B62 mol- These epitopes were endogenously processed and are human papilloma virus-type specific. To evaluate whether these CD8 T cell epitopes may be similar enough to potential epitopes from other high-risk Human Papilloma virus types, recognition of homologous peptides by the SEQ ID NO. 1 (E6 75-83) or SEQ ID NO. 2 (E6 133-142) specific T cell clones was examined (Tables 2 and 3). The SEQ ID NO. 1 (E6 75-83) or SEQ ID NO. 2 (E6 132-142) specific T cell clones did not recognize these epitopes demonstrating that they are Human Papilloma virus type-specific.

TABLE 2

Amino acid sequences of peptides of high-risk Human Papilloma virus types homologous to SEQ ID NO. 1 (E6 75-83) CD8 T cell epitope.

| Human Papilloma virus Type | Amino Acid Sequence | Position | Sequence Length (aa) | SEQ ID NO: |
|---|---|---|---|---|
| HPV16 | KFYSKISEY | 75-83 | 9 | 1 |
| HPV33 | RFLSKISEY | 68-76 | 9 | 8 |
| HPV51 | LFYSKIREY | 68-76 | 9 | 9 |
| HPV52 | RFLSKISEY | 68-76 | 9 | 10 |
| HPV56 | LFYSKVRKY | 71-79 | 9 | 11 |
| HPV73 | KFYSKIREY | 69-77 | 9 | 12 |

Bolded amino acid residues are different from those in HPV E6 75-83 CD8 T cell epitope.

TABLE 3

Amino acid sequences of peptides of high-risk Human Papilloma virus types homologous to SEQ ID NO. 2 (E6 133-142) CD8 T cell epitope.

| Human Papilloma Virus Type | Amino Acid Sequence | Position | Sequence Length (aa) | SEQ ID NO: |
|---|---|---|---|---|
| HPV16 | HNIRGRWTGR | 133-142 | 10 | 2 |
| HPV31 | HNIGGRWTGR | 126-135 | 10 | 13 |
| HPV33 | HNISGRWAGR | 126-135 | 10 | 14 |
| HPV51 | ANCWQRTRQR | 137-146 | 10 | 15 |
| HPV52 | HNIMGRWTGR | 126-135 | 10 | 16 |
| HPV58 | HNISGRWTGR | 126-135 | 10 | 17 |

Bolded amino acid residues are different from those in SEQ ID NO. 2 (E6 133-142) CD8 T cell epitope.

Memory T cells play an important role in maintaining long-term immunity to previously encountered pathogens or tumor antigens. They may proliferate, rapidly acquire effector functions to kill virus-infected cells or tumor cells and secrete cytokines that inhibit replication of the pathogen after re-stimulation with re-exposure to antigen (33). The identification of HPV16 E6 132-142 specific memory T cells was examined using tetramer staining on cells obtained from drawn blood samples obtained after HPV16 clearance, and before isolation of the T cell clones. The frequencies of tetramer$^+$CD8$^+$ T cells were above the negative control in three of the five samples. Upon peptide-stimulation in vitro for ten days, the frequencies of tetramer$^+$CD8$^+$ T cells expanded in two of the three samples, and almost all the epitope-specific T cells expressed the phenotype of memory T cell CD45RO$^+$ (Table 4).

TABLE 4

The reciprocal frequency of Human Leukocyte Antigen-A68/HPV16

| Months after Human Papilloma virus clearance | Peripheral blood mononuclear cells (%) | Peptide-stimulated peripheral blood mononuclear cells (%) † |
|---|---|---|
| 4 | 2,146 (0.047) | 512 (0.2) |
| 22 | 3,116 (0.032) | 510 (0.2) |
| 27 | 5,002 (0.020) | 11,572 (0.0086) |
| 48 | 5,214 (0.019) | 19,350 (0.0052) |
| 74 | 2,311 (0.043) | 10,209 (0.0098) |
| Positive control | 11 (9.0) | 8 (12.6) |
| Negative control | 5,010 (0.020) | 11,939 (0.0084) |

† Peripheral blood mononuclear cells were stimulated with SEQ ID NO. 2 (E6 133-142) for ten days before analysis.

Since this method of in vitro stimulation is used to increase the number of memory T cells, the data indicates the Human Papilloma virus-specific T cells can be detected at 22 months, or almost 2 years, after the Human Papilloma virus-DNA has become undetectable. It may be that the SEQ ID NO. 2 (E6 133-142) specific T cells were isolated 78 months after HPV16 clearance because mature dendritic cells, which are the most potent antigen presenting cells, were used for in vitro stimulation. The challenge in the future is to determine whether these memory cells confer long-term protection to Human Papilloma virus re-infection and whether these memory T cells are capable of quickly differentiating into a potent effector response during Human Papilloma virus re-infection.

TABLE 5

| Epitope | Sequence | SEQ ID NO: | HLA | U.S. Phenotype (%) ~ | | | |
|---|---|---|---|---|---|---|---|
| | | | | Cauc. | Afr. Amer. | Hisp. | Asian |
| E6(11-19) | KLPQLCTEL | 18 | A2 | 50.7 | 26.7 | 65.8 | 54.3* |
| E6(29-37) | TIHDIILEC | 19 | B48 | 0.0 | 0.0 | 7.3 | 7.6 |
| E6(29-38) | TIHDIILECV | 20 | A2 | 50.7 | 26.7 | 65.8 | 54.3* |
| E6(31-38) | HDIILECV | 21 | B61 | 2.4 | 0.0 | 7.3 | 6.4 |
| E6(49-57) | VYDFAFRDL | 22 | A24 | 21.3 | 8.9 | 24.4^ | 48.0* |
| E6(52-61) | FAFRDLCIVY | 23 | B57 | 7.0 | 6.4 | 2.4 | 2.6* |
| E6(52-61) | FAFRDLCIVY | 23 | B35 | 20.9 | 11.7 | 26.8 | 10.6* |
| E6(75-83) | KFYSKISEY | 1 | B62 | 10.8 | 3.2 | 5.6 | 9.4 |
| E6(80-88) | ISEYRHYCY | 24 | B18 | 4.6 | 8.5 | 12.2^ | 1.8* |
| E6(133-142) | HNIRGRWTGR | 2 | A68 | 4.4 | 15.8 | 29.2^ | 2.6* |
| E7(7-15) | TLHEYMLDL | 25 | A2 | 50.7 | 26.7 | 65.8 | 54.3* |
| E7(7-15) | TLHEYMLDL | 25 | B8 | 22.5 | 12.8 | 4.9 | 2.8 |
| E7(7-15) | TLHEYMLDL | 25 | B48 | 0.0 | 0.0 | 7.3 | 7.6 |
| E7(11-20) | YMLDLQPETT | 26 | A2 | 50.7 | 26.7 | 65.8 | 54.3* |
| E7(79-87) | LEDLLMGTL | 27 | B60 | 12.4 | 4.2 | 3.0 | 18.4 |
| E7(44-52) | QAEPDRAHY | 28 | B18 | | | | |
| | | | Cuml | 100 | 98.2 | 100 | 100 |

Thus, considerable effort has been made to identify antigenic epitopes of Human Papilloma virus. However, the present invention differs from others in that the approach has an advantage of being able to select T cell epitopes based on the magnitude of the T cell response. Hence, these epitopes may play a significant role in viral clearance. Additionally, the present invention studied women who demonstrated Human Papilloma virus clearance and identified several dominant CD8 T cell epitopes and regions of multiple T cell epitopes, which are relevant to approximately 99% of the U.S. population. Table 5 shows the CD8 T-cell epitopes contained in the HPV 16 E6 and E7 epitope hot spots. Taken together, SEQ ID NO. 1 through SEQ ID NO. 7 E6 peptides are immunodominant regions in which several T cell epitopes are contained. It is contemplated that one may determine whether these memory cells confer long-term protection to Human Papilloma virus re-infection and whether these memory T-cells are capable of differentiating into a effector response during Human Papilloma virus re-infection.

The method in the present invention used to identify the Human Papilloma virus SEQ ID NO. 1 (E6 75-83) and SEQ ID NO. 2 (E6 133-142) epitopes and Human Papilloma virus regions of multiple epitopes SEQ ID NO. 3 (E6 49-61), SEQ ID NO. 4 (E6 75-88), SEQ ID NO. 5 (E6 127-142), SEQ ID NO. 6 (E6 11-38), and SEQ ID NO. 7 (E6 49-88) incorporated key technical advances, which make it feasible to identify new epitopes even when particular T lymphocytes with the specificity may be relatively infrequent. These advances included (i) use of overlapping 15-mer peptides covering the entire protein to identify the region in which the epitope is contained; (ii) magnetically selecting for interferon-γ-secreting epitope peptide-specific T lymphocytes and (iii) seeding autologous and allogeneic Epstein-Barr Virus-transformed B-lymphoblastoid cell line cells for the enzyme-linked immunospot assay, thereby minimizing the number of T cell clone cells required to 1000 cells per well.

The present invention is directed to a method of determining a pattern of immunodominant T cell epitopes within a protein expressed in an individual, comprising: establishing T cell lines from an individual by stimulating in vitro the individual's immune cells with autologous dendritic cells which had been previously incubated with Human Papilloma virus protein or Human Papilloma virus peptides; further incubating the stimulated T cell line with peptides representing the Human Papilloma virus protein; determining the T cell response in the incubated cells; and identifying peptides that induce a specific T cell response, wherein a sequence of the peptide corresponds to a region within the protein, thereby determining the pattern of the immunodominant T cell epitopes within the protein in the individual.

Generally, a set of peptides is 15-amino acid residues long and overlaps by the 10 central amino acids and is representative of the entire protein. These peptides allow identification of what comprises the immunodominant T cell epitope. These peptides are used to select T cell lines based on the secretion of interferon-γ. Specifically, these peptides are fragments of Human Papilloma virus protein having amino acid sequence of SEQ ID NO. 1 (E6 75-83), SEQ ID NO. 2 (E6 133-142), SEQ ID NO. 3 (E6 49-61), SEQ ID NO. 4 (E6 75-88), SEQ ID NO. 5 (E6 127-142), SEQ ID NO. 6 (E6 11-38), and SEQ ID NO. 7 (E6 49-88); or have amino acid sequences of these peptides comprising at least 80% and up to and including 90% similarity of the composition of the immunodominant T cell epitopes in Human Papilloma virus protein of amino acid sequences SEQ ID NO: 1, SEQ ID NO: 2, SEQ ID NO: 3, SEQ ID NO: 4, SEQ ID NO: 5, SEQ ID NO: 6, and SEQ ID NO: 7 (Table 1).

Hence, the present invention contemplates investigating human papilloma virus epitopes as tumor antigens and using them as sources of antigens for dendritic cell immunotherapies or as a therapeutic vaccine to treat cervical cancer patients who express the particular Human Leukocyte Antigen types. The small size of these epitopes makes it easier to produce a large quantity of the antigen at Good Manufacturing Practice grade compared to a whole protein. Additionally, it is safer to use these epitopes in the treatment since the small size of the peptide makes it unlikely to have oncogenic potential. It is further contemplated to identify a large number of similar epitopes restricted by a wide variety of Human Leukocyte Antigen types, to be used either singly or together in concert, to develop a preventative vaccine, which could be used for the general population. Such a vaccine might comprise use of recombinant viral vector, a plasmid or a peptide.

Generally, such methods can be performed on an individual who is diagnosed with a pathophysiological condition, is in remission, or is diagnosed with a precursor of the pathophysiological condition. Examples of such pathophysiological conditions include but are not limited to a neoplastic disease or disorder, an autoimmune disease or disorder, or a pathogen-related infection or disease. Further, examples of the neoplastic disease include but are not limited to prostate cancer, ovarian cancer, or cervical cancer. In the case of cervical cancer, the individual might have been infected with Human Papilloma virus, had atypical cells of undetermined significance (ACUS), had abnormal pap smear results, or had been diagnosed with precursor of cervical cancer for example, squamous intraepithelial lesion. Although the present invention used the method to identify immunodominant epitopes of Human Papilloma virus protein, this method may be used to identify dominant epitopes of any protein such as prostate specific antigen or cancer antigen-125 or Human Immunodeficiency virus or malaria or melanoma as long as the protein or peptides can be cloned into a recombinant virus that can infect dendritic cells. Therefore, this method can be used to identify epitopes from many other pathogens or self-antigens.

Furthermore, the present invention is contemplated for use as an immunogenic composition comprising a sequence or a combination of sequences identified herein and an immunogenic composition comprising an adjuvant to enhance the immune response in said individuals. Such a peptide sequence may be acetylated at the amino terminus, amidated at the carboxyl terminus or acetylated at the amino terminus and amidated at the carboxyl terminus. Such a sequence or sequences may be expressed in a recombinant viral vector, a plasmid or a peptide. Representative adjuvants comprises antigens from *Candida albicans*, mumps, or *Trichophyton*. Such an adjuvant can also be nanoemulsions or nanoparticles. Such an adjuvant includes, but is not limited, to concentrated whole cell extract made from lyophilized cells of *Candida albicans*. Such an adjuvant is contained in a composition in an antigen/adjuvant ratio of about 20 micrograms antigen per 200 microliter of adjuvant to about 20 micrograms antigen per 500 microliter of adjuvant. Such an immunogenic composition may be administered intradermally.

The present invention is directed to a method of determining immunodominant T cell epitopes within a protein expressed in an individual, comprising: pulsing dendritic cells obtained from the individual with a recombinant protein, establishing T cell lines by stimulating peripheral blood mononuclear cells (PBMCs) with the dendritic cells, incubating the T cells with peptides representative of the protein, measuring the specific T cell response in the incubated cells and identifying peptides that induce T cell response, where sequence of the peptide corresponds to a region within the protein, thereby determining the immunodominant T cell epitopes within the protein in the individual. This method may further comprise determining the amino acid sequence of the immunodominant T cell epitope identified therein. In general, the individual may include but is not limited to one who is diagnosed with a pathophysiological disorder, is in remission, or is diagnosed with a precursor of the pathophysiological condition.

Further, the pathophysiological condition may include but is not limited to a neoplastic disease or disorder, an autoimmune disease or disorder or a pathogen-related disease. Examples of the neoplastic disease or disorder may include but is not limited to Human Papilloma virus infection, atypical cells of undetermined significance (ACUS), squamous intraepithelial lesion, cervical intraepithelial lesion, cervical cancer, prostate cancer, ovarian cancer, vulvar cancer, anal cancer, head cancer, neck cancer or other types of cancer. Additionally, the T cell epitopes determined by this method may be CD4 T cell epitopes or CD8 T cell epitopes. Still further, the peptides that comprise the immunodominant T cell epitopes may have amino acid sequence of SEQ ID NO: 1, SEQ ID NO: 2, SEQ ID NO: 3, SEQ ID NO: 4, SEQ ID NO: 5, SEQ ID NO: 6 and SEQ ID NO: 7; or have amino acid sequences of these peptides comprising at least 80% and up to and including 90% similarity of the composition of the immunodominant T cell epitopes in Human Papilloma virus protein of amino acid sequences SEQ ID NO. 1, SEQ ID NO. 2, SEQ ID NO. 3, SEQ ID NO. 4; SEQ ID NO. 5; SEQ ID NO. 6; SEQ ID NO. 7, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or SEQ ID NO: 37 (Tables 1 and 6-7, and FIG. 5).

The present invention is further directed to a method of immunotherapy targeted towards a protein in an individual, comprising: isolating immune cells from the individual; incubating the isolated immune cells with peptide comprising one or more of the immunodominant T cell epitope identified using the method described supra; and transferring the incubated immune cells back into the individual such that the immune cells induce a specific immune response in the individual, thus generating immunotherapy targeted towards the protein in the individual. Such a peptide may be acetylated at the amino terminus, amidated at the carboxyl terminus or acetylated at the amino terminus and amidated at the carboxyl terminus. Specifically, the protein towards which the immunotherapy is targeted may include but is not limited to a Human Papilloma virus E6 or E7 protein. The immune cells used in this method may be T cells or dendritic cells. The individual likely to benefit from this immunotherapy may include but is not limited to one who has abnormal pap smear results has been diagnosed with precursor of cervical cancer, has been diagnosed with cervical cancer or is suspected or at risk of suffering from cervical cancer. Since antigenic epitopes for many other pathogens and self antigens can be identified using the method described in the present invention, the immunotherapy described above will benefit individuals suffering from other cancers, pathogen-related diseases and autoimmune diseases.

The present invention is also directed to synthetic peptides having a sequence selected from the group consisting of SEQ ID NO. 1, SEQ ID NO. 2, SEQ ID NO. 3, SEQ ID NO. 4; SEQ ID NO. 5; SEQ ID NO. 6; SEQ ID NO. 7, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or SEQ ID NO: 37; or have amino acid sequences of these peptides comprising at least 80% and up to and including 90% similarity of the amino acid sequences SEQ ID NO. 1, SEQ ID NO. 2, SEQ ID NO. 3, SEQ ID NO. 4; SEQ ID NO. 5; SEQ ID NO. 6; SEQ ID NO. 7, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or SEQ ID NO: 37 (Tables 1 and 6-7, and FIG. 5).

Furthermore, the present invention is further directed to an immunogenic composition comprising one or more of the synthetic peptides identified herein. Such synthetic peptides may be acetylated at the amino terminus, amidated at the carboxyl terminus or acetylated at the amino terminus and amidated at the carboxyl terminus. Such an immunogenic composition may also comprise an adjuvant to enhance the immune response in the individuals. Such a sequence or sequences may be expressed in a recombinant viral vector, a plasmid or a peptide. Such an adjuvant comprises antigens from Candida albicans, mumps, or Trichophyton. Such an adjuvant can also be nanoemulsions or nanoparticles. Such an adjuvant includes, but is not limited, to concentrated whole cell extract made from lyophilized cells of Candida albicans. Such an adjuvant is contained in a composition in an antigen/adjuvant ratio of about 20 micrograms antigen per 200 microliter of adjuvant to about 20 micrograms antigen per 500 microliter of adjuvant. Such an immunogenic composition may be administered intradermally.

Additionally, the present invention is also directed to a method of preventing or treating a pathophysiological condition involving expression of a protein in an individual, comprising administering an immunologically effective amount of the immunogenic composition described herein to the individual, where the composition activates a specific immune response in the individual, thereby preventing or treating the pathophysiological condition in the individual. Generally, the individual who might benefit from this method may include but is not limited to one who has Human Papilloma virus infection, one who has atypical cells of undetermined significance, one who has abnormal pap smear results, one who has been diagnosed with a precursor of cervical cancer such as squamous intraepithelial lesion or is suspected or at risk of suffering from cervical cancer. The cancer may include but is not limited to one that is Human Papilloma virus positive.

Furthermore, the present invention is directed to a method for increasing regression of Human Papilloma Virus (HPV)-associated cervical lesions in an HPV positive individual, comprising administering an immunogenic composition comprising two or more peptides derived from two or more immunodominant epitopes of HPV E6 or E7 protein effective to generate CD8 T-cell responses specific against the HPV thereby increasing regression of the cervical lesions. Such immunogenic peptides are acetylated at the amino terminus, amidated at the carboxyl terminus or acetylated at the amino terminus and amidated at the carboxyl terminus. The immunogenic composition may further comprise an adjuvant, such as, but not limited to, antigens from Candida albicans, antigens from mumps, antigens from Trichophyton, a nanoemulsion or nanoparticles. Such an adjuvant includes, but is not limited, to concentrated whole cell extract made from lyophilized cells of Candida albicans. Also, the immunogenic composition may be expressed in a recombinant viral vector, a plasmid or as a peptide. The immunodominant epitopes may include, but are not limited to, a sequence shown in SEQ ID NOs: 29-37. The HPV type may be HPV 16 or HPV 16 related types or HPV 18. Such adjuvant is contained in the composition in an antigen/adjuvant ratio of about 20 micrograms antigen per 200 microliter of adjuvant to about 20 micrograms antigen per 500 microliter of adjuvant. Such immunogenic composition may be administered intradermally.

Additionally, the present invention is also directed to a method to predict the probability of developing persistent cervical neoplasia in an individual, consisting the steps of: 1) obtaining whole blood from the individual; 2) establishing mature dendritic cells by pulsing the dendritic cells from the whole blood with a peptide fragment of an E6 protein of a Human Papilloma Virus; 3) establishing a T cell line by combining T cells from the whole blood with the mature dendritic cells; 4) determining the percentage of T cells in the T cell line that respond to a peptide fragment of an E6 protein of a Human Papilloma Virus. In such a method, a higher T cell response to the peptide fragment mentioned supra from the individual being diagnosed than a T cell response to the same peptide fragment from an individual without cervical neoplasia indicates that the individual with higher T cell response is more likely to develop persistent cervical neoplasia. The individual undertaking the diagnosis includes, but is not limited to, an individual who has an abnormal Papanicolaou smear or is suspected to have cervical neoplasia. The peptide fragment of an E6 protein of a Human Papilloma Virus used in the diagnosis method includes, but is not limited to, a peptide fragment of an E6 protein of a Human Papilloma Virus type 16. The peptide fragment of an E6 protein of a Human Papilloma Virus used in the diagnosis method includes, but is not limited to, a peptide sequence having at least 80% identical to a sequence that is SEQ ID NO. 1, SEQ ID NO. 2, SEQ ID NO. 3, SEQ ID NO. 4; SEQ ID NO. 5; SEQ ID NO. 6; SEQ ID NO. 7, SEQ ID NO: 29, SEQ ID NO: 31, SEQ ID NO: 32, SEQ ID NO: 33, SEQ ID NO: 34, SEQ ID NO: 35, SEQ ID NO: 36, or SEQ ID NO: 37. The T cells used in the diagnosis method includes, but is not limited to, CD4 positive T cells.

The immunogenic compositions disclosed herein may be administered either alone or in combination with another drug or a compound. Such a drug or a compound may be administered concurrently or sequentially with the immunogenic composition. The effect of co-administration with the immunogenic composition is to lower the dosage of the drug or the compound normally required that is known to have at least a minimal pharmacological or therapeutic effect against the disease that is being treated. Concomitantly, toxicity of the drug or the compound to normal cells, tissues and organs is reduced without reducing, ameliorating, eliminating or otherwise interfering with any cytotoxic, cytostatic, apoptotic or other killing or inhibitory therapeutic effect of the drug or the compound.

The composition described herein and the drug or compound may be administered independently, either systemically or locally, by any method standard in the art, for example, subcutaneously, parenterally, intraperitoneally, intradermally, intramuscularly, topically, nasally, or by inhalation spray, by drug pump or contained within transdermal patch or an implant. Dosage formulations of the composition described herein may comprise conventional non-toxic, physiologically or pharmaceutically acceptable carriers, or vehicles suitable for the method of administration.

The immunogenic composition described herein and the drug or compound may be administered independently one or more times to achieve, maintain or improve upon a therapeutic effect. It is well within the skill of an artisan to determine dosage or whether a suitable dosage of either or both of the immunogenic composition and the drug or compound comprises a single administered dose or multiple administered doses.

As is well known in the art, a specific dose level of such an immunogenic composition for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, and general safety and purity standards as required by Food and Drug Administration Office of Biologics standards.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Subjects and Cells

The generation of CD8 T-cell lines from women who were able to clear their Human Papilloma virus infections has been described (Nakagawa et al., 2005). Briefly, the CD8 T-cell lines were established by stimulation peripheral blood mononuclear cells using autologous dendritic cells infected with recombinant vaccinia viruses expressing the HPV 16 E6 protein. Using enzyme-linked immunospot assay, the presence of potential CD8 T-cell epitopes in the E6 31-55 and E6 61-85 regions was demonstrated for subject 2, and that in the E6 31-55, E6 76-100, E6 121-145 regions for subject 18. The blood samples used to establish these CD8 T-cell lines were drawn 53 or 78 months after HPV 16 clearance in subjects 2 or 18 respectively. These findings were extended by defining the minimal/optimal amino acid sequences and the Human Leukocyte Antigen restriction molecules of the CD8 T-cell epitopes.

Example 2

Synthetic HPV Peptides

A series of 15-mer peptides overlapping each other by 10 amino acids and a series of 9-mer peptides overlapping each other by 8 amino acids covering the HPV 16 E6 protein have been described (37). To define the minimal and optimal amino acids sequences of the CD8 T-cell epitope, 8-mer, 10-mer, 11-mer, and homologous peptides were synthesized (CPC Scientific, Inc, San Jose, Calif.). All peptides were dissolved in small amounts of dimethylsulfoxide (~50 μl), diluted to 5 mM with phosphate buffered saline, and kept frozen at −80° C. until final dilution for their use in the assay.

Example 3

Isolation of Antigen-Specific T-Cell Clones after Magnetic Selection of Interferon-γ Secreting Cells The CD8 T cell lines from subjects 2 and 18 were stimulated for two additional 7-day cycles to increase the frequency of targeted antigen specific T-cells as described (37). The HPV 16 E6 antigen-specific CD8 T-cell lines (~2×10$^7$ cells from each line) were then stimulated with 10 μM of each peptide contained in positive peptide pools (three 15-mer peptides contained in each peptide pool) for 3-6 h. Following this incubation, the interferon-γ secreting cells were selected using a commercially available kit according to the manufacturer's instructions (Interferon-γ Secretion Assay, Miltenyi Biotec).

To isolate HPV 16 E6 peptide-specific T-cell clones, interferon-γ positive T-cells were plated at a 0.5 cell/well concentration in a 0.5× feeder cell mixture [Yssel's medium containing 1% human serum, penicillin G 100 U/ml, streptomycin 100 µg/ml, $5 \times 10^5$/ml irradiated allogeneic peripheral blood mononuclear cells $5 \times 10^4$/ml irradiated JY cells, phytohaemagglutinin at a concentration of 0.1 µg/ml] and incubated at 37° C. 5% $CO_2$. On Day 5, 100 µl of Yssel's medium with 20 u/ml of recombinant human interleukin-2 was added to each well. After identification of growing T-cell clones, the cells were transferred to a well of a 24-wells plate containing 1 ml of 1× feeder cell mixture (Yessel's medium, $1 \times 10^6$/ml irradiated allogeneic peripheral blood mononuclear cells, $1 \times 10^5$/ml irradiated JY cells, 0.1 µg/ml phytohaemagglutinin). Growing cultures were split using Yssel's medium containing 20 u/ml of recombinant IL-2 for enzyme-linked immunospot assay screening assay.

Example 4

Enzyme-Linked Immunospot Assay for Screening T-Cell Clones

Cells secreting interferon-γ in an antigen-specific manner were detected by enzyme-linked immunospot assays. A 96-wells plate (MultiScreen; Millipore, Bedford, Mass.) was coated with primary anti-interferon-γ monoclonal antibody, 1-DIK (Mabtech, Stockholm, Sweden) at a concentration of 5 µg/ml overnight at 4° C. The plate was washed 4 times with phosphate-buffered saline and blocked with 50 µl RPMI 1640 medium supplement with 5% human serum for 1 hr at 37° C. One-hundred thousand autologous Epstein-Barr Virus-transformed B-lymphoblastoid cell line cells were added to all wells. Media containing T-clone cells was plated to one well at the same position in triplicate (to test two peptide pools and media only control for subject 2) or in quadruplicate (to test three peptide pools and media only control for subject 18) plates. The final concentration was 10 µM for each peptide). One phytohaemagglutinin (10 µg/ml) as a positive control and one without T-clone cells as a negative control was included on each plate. After 20 hr incubation, wells were washed 4 times with phosphate buffered saline containing 0.05% Tween-20.

A total of 50 µl biotin-conjugated anti-interferon-γ monoclonal antibody (1 µg/ml, Mabtech) was added to each well and incubated for 2 hr at 37° C. After washing the plate with phosphate buffered saline containing 0.1% Tween-20 four times, 50 µl of Avidin-bound biotinylated horseradish peroxidase H (Vectastain Elite Kit; Vector laboratories, Inc., Burlingame, Calif.) was added to each well and the plate was incubated for 1 hr at 37° C. Wells were washed with phosphate buffered saline containing 0.1% Tween-20 for 4 times and spots were developed using stable diaminobenzene (Research Genetics, Huntsville, Ala.) at room temperature. Wells were washed 3 times with deionized water and air-dried. Spot-forming units were counted using an automated enzyme-linked immunospot assay analyzer (Cell Technology, Inc., Jessup, Md.). The wells that showed spots in an enzyme-linked immunospot assay plate with one peptide pool, yet not in other plates, were considered to potentially contain T-cell clones with specificity of interest.

Example 5

Epstein-Barr Virus-Transformed B-Lymphoblastoid Cell Line Cells

An Epstein-Barr virus-transformed B-lymphoblastoid cell line is established for each subject that CD8 T cell epitopes are characterized (38). In short, CD3- and CD14-depleted peripheral blood mononuclear cells are incubated, with occasional mixing, for 90 minutes with a supernatant fluid of B958 containing free Epstein-Barr virus virions. Ninety percent of Epstein-Barr virus virions are removed by centrifugation, and the peripheral blood mononuclear cells are grown in RPMI 1640 containing 10% fetal calf serum, penicillin G (1,000 U/mL), streptomycin (1,000 µg/mL), and cyclosporin A. The peripheral blood mononuclear cells are incubated and monitored for growth of characteristic cell clumps. Once a stable Epstein-Barr virus-transformed B-lymphoblastoid cell line is established, it is cryopreserved to prevent loss due to contamination. Epstein-Barr virus-transformed B-lymphoblastoid cell line cells are utilized to reduce the number of T cell clones necessary to define the minimal/optimal amino acid sequences and the restriction element of the T cell epitope.

Example 6

Enzyme-Linked Immunospot Assays to Characterize the CD8 T-Cell Epitopes of HPV 16 E6 Protein To confirm the specificity of the potential-epitope positive T-cell clones identified in screening, enzyme-linked immunospot assays were repeated using 15-mer peptides contained in the positive peptide pools individually in duplicate or triplicate. One thousand T-clone cells were co-incubated with $1 \times 10^5$ autologous Epstein-Barr Virus-transformed B-lymphoblastoid cell line cells along with 20 U/ml of recombinant human IL-2 in the presence of 15-mer peptide at a concentration of 10 µM. The enzyme-linked immunospot assays were otherwise performed as described above. To determine the minimal and optimal amino acid sequences of the CD8 T-cell epitopes, additional enzyme-linked immunospot assays were performed using peptides of various lengths. Serial dilutions of these peptides were also performed whenever necessary as described. A peptide of a particular length was considered optimal if noticeably larger numbers of spot forming units were observed at multiple concentrations.

To determine whether the HPV 16 E6 epitopes were being endogenously processed, autologous Epstein-Barr Virus-transformed B-lymphoblastoid cell line cells infected with recombinant vaccinia virus expressing the E6 protein (E6-vac) at a multiplicity of infection of 5 were used as antigen-presenting cells in enzyme-linked immunospot assays. The wild-type virus, Western Reserve (WR), and/or recombinant vaccinia virus expressing HPV 16 E7 (E7-vac) served as negative controls. Otherwise, enzyme-linked immunospot assays were carried out as described above. Human Leukocyte Antigen typing was performed by serological method or sequence-specific primers and polymerase chain reaction method.

Example 7

Identification of the Restricting Human Leukocyte Antigen Class I Molecules

To identify putative restricting Human Leukocyte Antigen class I molecule, enzyme-linked immunospot assays were performed, as described above, using autologous Epstein-Barr Virus-transformed B-lymphoblastoid cell line cells sharing one or a few class I molecules with the subjects. The results were confirmed using chromium release assays in which at least two autologous Epstein-Barr Virus-transformed B-lymphoblastoid cell line cells expressing the putative Human Leukocyte Antigen class I molecule were tested. The Epstein-Barr Virus-transformed B-lymphoblastoid cell line cells were labeled with 100 µCi of sodium chromate ($Na_2{}^{51}CrO_4$), and were incubated with 10 µM of positive peptide. After plating the cells in 96-wells plate at $3\times10^3$/well, effector cells were added at multiple effector to target cell (E:T) ratios. After 5 hr of incubation, the supernatants were harvested and radioactivity was counted with a gamma counter (Packard Instruments, Meriden, Conn.). Percentage specific lysis was calculated as described (39).

Example 8

Characterizing the Surface Phenotypes of the T-Cell Clones $5\times10^5$ T-clone cells were stained with CD4-PE/CD8-FITC cocktail, CD3-FITC/CD16-PE cocktail and corresponding antibody isotype controls (Caltag, Burlingame, Calif.) for 30 min at 4° C. The cells were washed with RPMI 1640 medium plus 5% fetal bovine serum, and resuspended in phosphate buffered saline containing 1% formalin. Events were analyzed using the Coulter EPICS XL-MLC flow cytometer (Beckman Coulter, Fullerton, Calif.).

Example 9

Identifying Homologous CD8 T-Cell Epitopes from Other High-Risk Human Papilloma Virus Types The utility of the newly described HPV16 E6 CD8 T-cell epitopes as the source of antigens for vaccine or immunotherapy would be broader if the specific T-cells also recognized homologous epitopes in other high-risk Human Papilloma virus types. Therefore, homologous epitopes, defined as peptides containing the same anchor residues (amino acid no. 2 and the last amino acid residue of the CD8 T-cell epitope) located within the 20-amino-acid region from the original HPV16 epitope, were identified by examining the protein sequences of the E6 proteins of HPV31, -33, -35, -39, -45, -51, -52, -56, -58, -59, -68, and -73 (http://hpv-web.lanl.gov/stdgen/virus/hpv/). The recognition of the homologous peptides by SEQ ID NO. 1 (E6 75-83) specific T-cells clones (1,000 cells of insert clones #s tested) were tested using Epstein-Barr Virus-transformed B-lymphoblastoid cell line cells ($1\times10^5$ cells per well) from subject 2 and Epstein-Barr Virus-transformed B-lymphoblastoid cell line cells ($1\times10^5$ cells per well) from five additional individuals expressing the HLA-B62 molecule.

Similarly, the recognition of the homologous peptides by SEQ ID NO. 2 (E6 133-142) specific T-cell clones (1,000 cells of insert clones #s tested) were tested using Epstein-Barr Virus-transformed B-lymphoblastoid cell line cells ($1\times10^5$ cells per well) from subject 18 and Epstein-Barr Virus-transformed B-lymphoblastoid cell line cells ($1\times10^5$ cells per well) from five more individuals expressing the HLA-A68 molecule. The SEQ ID NO. 1 (E6 75-83) or SEQ ID NO. 2 (E6 133-142) peptides were used as a positive control. Peptides were added at a concentration of 10 µM along with 20 U/ml of recombinant IL-2, and the wells were set up in duplicate or triplicate. The enzyme-linked immunospot assay was performed as described above.

Example 10

Detection of HPV 16 E6 133-142 Specific Memory T-Cells Using Tetramer Analysis

During the process of stimulating and isolating epitope-specific T-cells clones, the CD8 T-cells from women who had cleared their HPV 16 infection were incubated with autologous mature dendritic cells infected with vaccinia virus expressing E6 protein since dendritic cells are the most potent antigen presenting cells. One drawback of this approach is that one cannot be certain whether the antigen-specific T-cells are primed during the course of their natural HPV 16 infection in vivo or during the course of the in vitro stimulation. If the former scenario is true, then the epitope-specific memory T-cells may be detectable in peripheral blood mononuclear cells from the same subjects. In order to assess this possibility, a tetramer designed to bind T-cells specific for the SEQ ID NO. 2 (E6 133-142) epitope restricted by the HLA-A6801 molecule was obtained from the National Institutes of Health tetramer facility. A tetramer could not be made for the other epitope restricted by the HLA-B62 molecule since this Human Leukocyte Antigen type was not available for production.

Peripheral blood mononuclear cells from subject 18 collected 4 months, 22 months, 27 months, 48 months, and 74 months after HPV 16 clearance were available for this analysis (FIGS. 1A-1B). These peripheral blood mononuclear cell samples were analyzed immediately after thawing and after in vitro stimulation in a manner known to enhance the number of memory T-cells. In short, cryopreserved peripheral blood mononuclear cells were thawed and incubated at $2\times10^6$/ml in medium (RPMI 1640 plus 10% human serum, penicillin 100 U/ml and streptomycin 100 µg/ml; referred to as RP-10H) overnight. Then, the cells were recounted and were incubated at $1\times10^6$ peripheral blood mononuclear cells/ml/well in the presence of SEQ ID NO. 2 (E6 133-142) peptide at a concentration of 10 µM (day 0).

After a 3 d incubation, recombinant human IL-2 was added to each well to a concentration of 1,800 U/ml. One more ml of RP-10H with recombinant human IL-2 (1,800 U/ml) was added to each well on day 7. Three days later (day 10), the cells were pooled and washed three times and cultured in RP-10H at $10^6$/ml (without peptide and recombinant human IL-2) in a 24-wells plate overnight, and the tetramer staining was performed on the following day.

The optimal amount of SEQ ID NO. 2 (E6 133-142) PE-labeled tetramer to be used was determined by serial dilution as recommended by the National Institutes of Health tetramer facility (1:50, 1:100, 1:200, 1:400, 1:800, 1:1600). The lowest concentration, 1:1600, was chosen because minimal amount of background staining was observed without decrease in the detection of the T-cell clones (#83-18, designates clone #83 from subject 18) used as positive control. Three different incubating conditions were tested (4° C. for 30 min, room temperature for 30 min, or 37° C. for 15 min), but no difference in staining was observed. Therefore, the standard condition for tetramer staining (i.e., room temperature for 30 min) was used.

In addition the peripheral blood mononuclear cell samples were stained with CD4-FITC, CD14-FITC, CD19-FITC, CD8-PerCP, and CD45RO-APC (BD Biosciences, San Jose, Calif.). Peripheral blood mononuclear cells from a healthy donor known to be HLA-A6801 negative were used as a negative control. T-cell clone cells (#83-18) were mixed with peripheral blood mononuclear cells from this negative control donor (10% T-cell clone cells), and used as the positive control.

The samples were analyzed using Becton Dickinson FAC-SCalibur (BD Bioscience). A lymphocyte gate was drawn in the forward and side scatters, and this population was further gated for CD4/14/19-FITC negativity to eliminate non-specific staining of CD4 T-cells, monocytes, and B-cells. One hundred thousand events were acquired per sample. The percentages of tetramer$^+$ CD8$^+$ T-cells were calculated by dividing the number of cells in the circle in the right upper corner (region determined using the positive control sample) by the sum of cell numbers in the upper right and lower right quadrants (CD8$^+$ T-cells) and the corresponding reciprocal frequencies were calculated. Whether these tetramer$^+$ CD8$^+$ T-cells were CD45RO$^+$ T-cells were also determined.

Example 11

Natural History of HPV 16 Infection in Subjects 2 and 18

The patterns of CD8 T-cell epitopes in women who had cleared their HPV 16 infection were described (37). Here, further characterizations of the T-cell responses in subjects 2 and 18 were performed. They were participants of a longitudinal study of Human Papilloma virus infection, and they were monitored using cervical Human Papilloma virus DNA testing by PCR, cytology, and colposcopy every 4 months. Subject 2's HPV 16 infection was detected at a single visit and the blood to establish the CD8 T-cell line was drawn 53 months later. On the other hand, subject 18 had an HPV 16 infection, which lasted for over 4 years, and the blood sample was taken 53 months after clearance (FIGS. 1A-1B).

Example 12

HPV 16 E6 71-85 Restricted by the HLA-B62 Molecule; the Dominant Epitope Characterized from Subject 2

Approximately $1.8 \times 10^4$ (0.09%) interferon-γ secreting cells were isolated from the CD8 T-cell line from subject 2 as described above. Limiting dilution analysis was performed to isolate T-cell clones and a total of 344 T-cell clones were expanded. A random selection of 94 T-cell clones were used for enzyme-linked immunospot assay screening, and eight T-cell clones (#8-2, #15-2, #40-2, #74-2, #76-2, #78-2, #93-2, #94-2) were positive for the peptide pool covering the HPV 16 E6 61-85 region (dominant peak), but none of the T-cell clones were positive for the peptide pool covering the E6 31-55 (subdominant peak).

When the enzyme-linked immunospot assay was repeated using individual 15-mer peptides, seven (#8-2, #15-2, #40-2, #74-2, #76-2, #78-2, #94-2) of the eight screen-positive T-cell clones were positive with the E6 71-85 peptide but not with the E6 61-75 and E6 66-80 peptides (FIG. 2A). To examine the nature of the antigen processing, vaccinia virus expressing E6 protein (E6-vac) or Western Reserve wild type vaccinia virus infected autologous Epstein-Barr Virus-transformed B-lymphoblastoid cell line cells were used as antigen presenting cells. The same seven T-cell clones positive for the E6 71-85 peptide were positive when tested with E6-vac infected Epstein-Barr Virus-transformed B-lymphoblastoid cell line cells suggesting that this E6 epitope is endogenously processed (FIG. 2B).

Figures 2C, 2D:
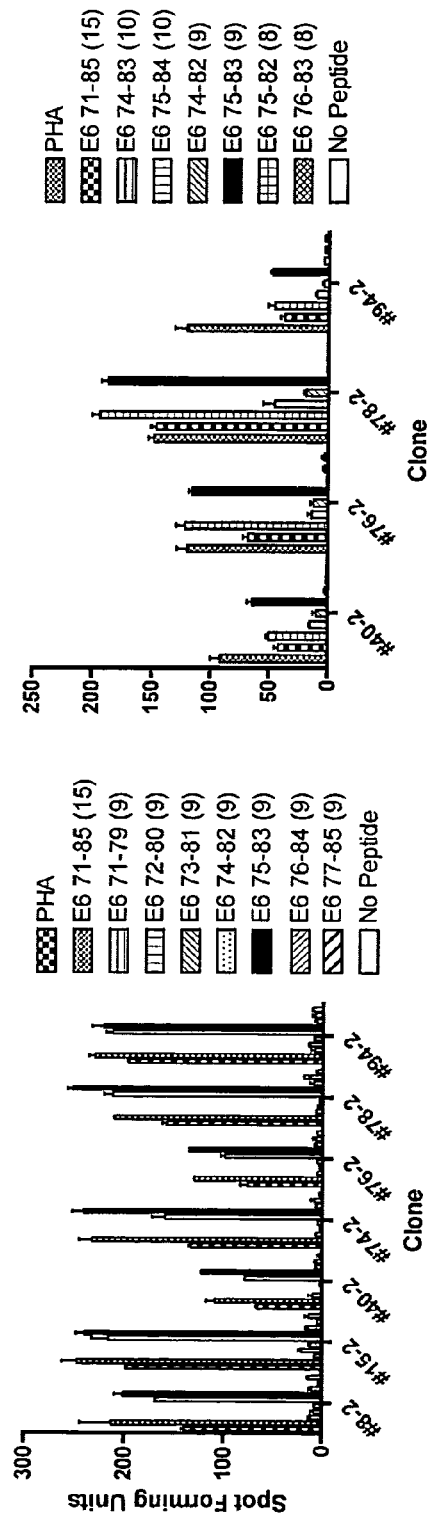
Figure 2F:
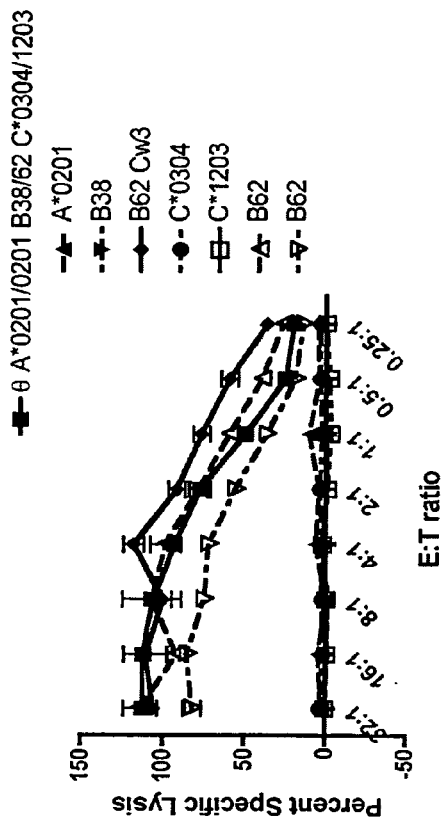
Figure 2E:
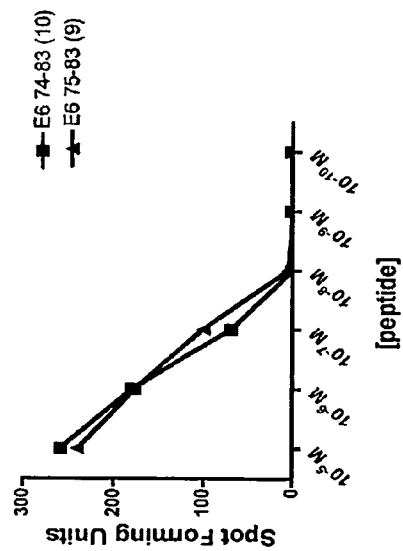

To determine the minimal and optimal epitope amino acid sequence, a series of enzyme-linked immunospot assays were performed (FIG. 2C-2E). Of the series of 9-mer peptides within the E6 71-85 peptide tested, the SEQ ID NO. 1 (E6 75-83) peptide showed the most number of spot forming units per well for all clones tested followed by the E6 74-82 peptide (FIG. 2C). When the two 10-mer peptides surrounding the SEQ ID NO. 1 (E6 75-83) peptide and two 8-mer peptides within were compared, the SEQ ID NO. 1 (E6 75-83) 9-mer peptide and the E6 74-83 10-mer peptide demonstrated comparable number of spot forming units for all T-cell clones tested (FIG. 2D). A serial dilution of these two peptides showed that they were equivalent over a wide-range of peptide concentration (FIG. 2E). Therefore, the SEQ ID NO. 1 E6 75-83 (9 amino acids) appeared to be the minimal and optimal sequence for this epitope.

To identify the Human Leukocyte Antigen restriction element of this novel epitope, a panel of allogeneic Epstein-Barr Virus-transformed B-lymphoblastoid cell line cells matched to one or more Human Leukocyte Antigen class I molecules of subject 2 were used in an enzyme-linked immunospot assay (clones #40-2, #76-2, #78-2, and #94-2 were tested). An allogeneic Epstein-Barr Virus-transformed B-lymphoblastoid cell line cells matched with the HLA-B62 molecule showed a positive response along with the autologous Epstein-Barr Virus-transformed B-lymphoblastoid cell line cells for all four T-cell clones tested. To confirm this result, a chromium release assay was performed with the T-cell clones (clones #76-2 and #78-2) as effectors and Epstein-Barr Virus-transformed B-lymphoblastoid cell line cells pulsed with the SEQ ID NO. 1 (E6 75-83) as targets (FIG. 2F). Three of the Epstein-Barr Virus-transformed B-lymphoblastoid cell line cells were allogeneic Epstein-Barr Virus-transformed B-lymphoblastoid cell line cells expressing the HLA-B62 molecule, and all of them were lysed by the T-cell clones confirming that the restriction element of the SEQ ID NO. 1 (E6 75-83) epitope is the HLA-B62 molecule.

Example 13

SEQ ID NO. 2 (E6 133-142) Restricted by the HLA-A6801 Molecule; the Dominant Epitope Characterized from Subject 18

From this subject, $6.5 \times 10^4$ (0.31%) interferon-β secreting cells were selected, and 504 of 1,048 T-cell clones that grew were expanded. A random selection of 94 T-cell clones was used for screening enzyme-linked immunospot assay. Sixty-four of 94 T-cell clones tested were positive for the E6 121-146 region (dominant peak), and none of them were positive for the E6 31-55 and E6 76-100 regions (subdominant peaks).

Figures 3A, 3B:
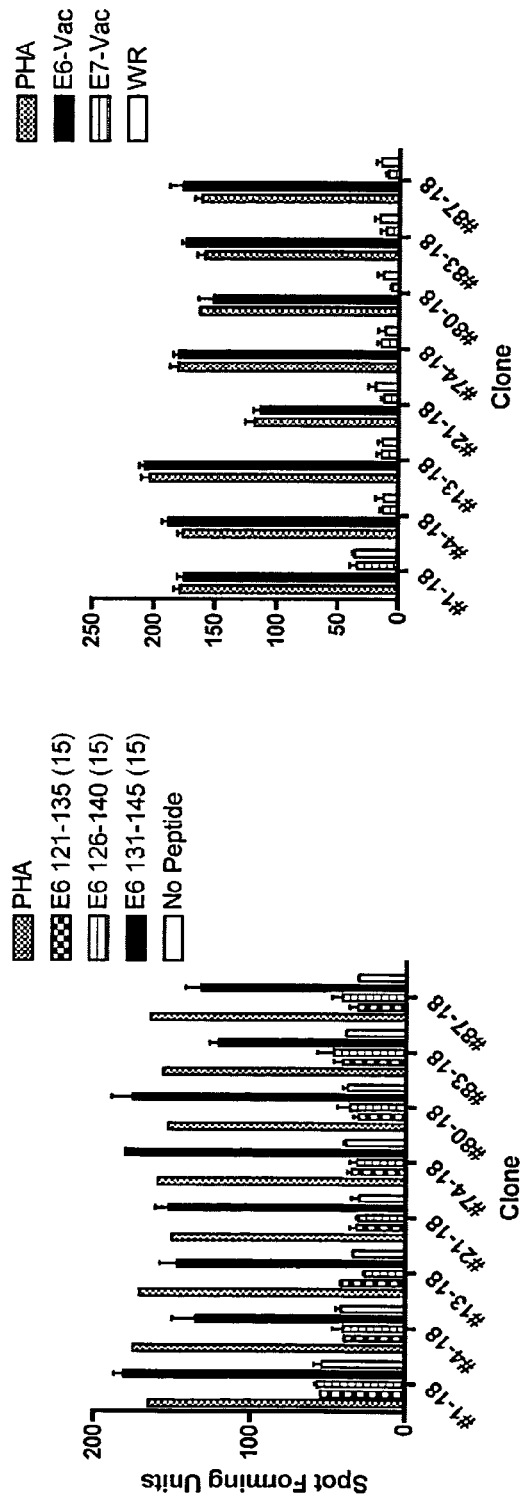
FIGS. 3A-3F show the characterization of the dominant CD8 T cell epitope of subject 18 in terms of its minimal and optimal amino acid sequence and the Human Leukocyte Antigen restricting molecule.
Figures 3C, 3D:
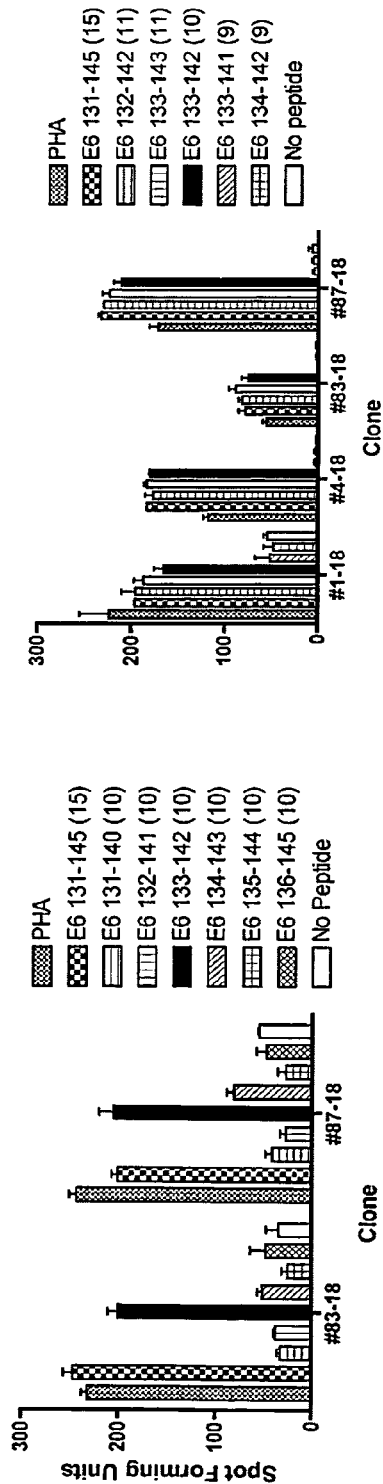
Figure 3F:
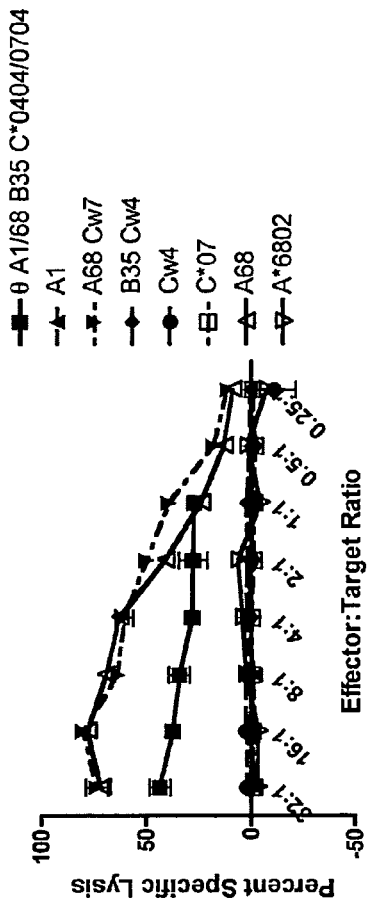
Figure 3E:
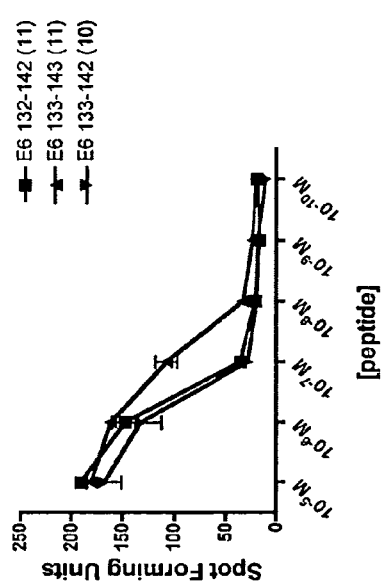
Figure 4:
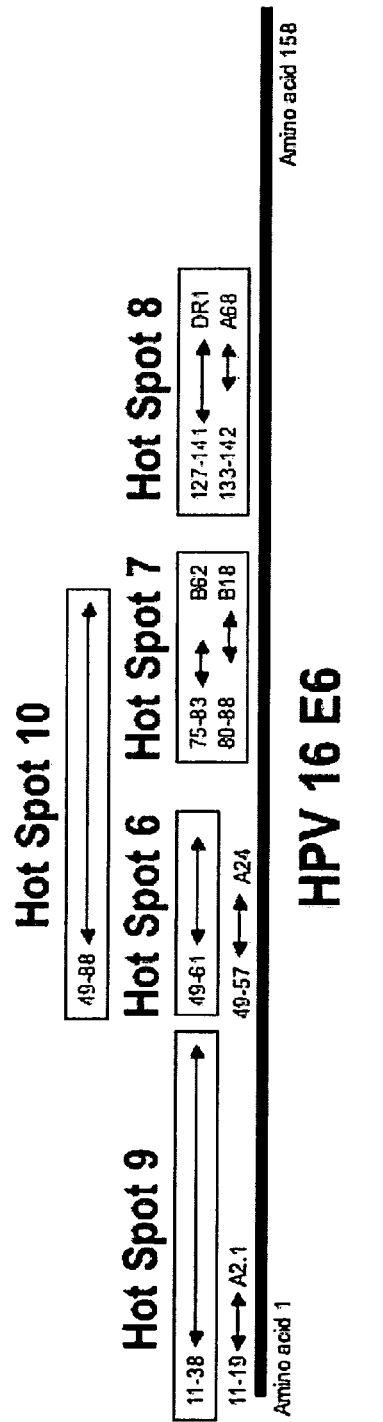
FIG. 4 shows T cell epitope "hot spots" identified in the HPV16 E6 protein. Regions of the Human Papilloma virus HPV16 E6 protein, which contain multiple T cell epitopes termed "hot spots", have been identified and shown to be restricted by several Human Leukocyte Antigen major histocompatibility complex I molecules. The CD8 T cell epitopes contained in these epitopes "hot spots" are relevant to 99% of the US population.

Eight (#1-18, #4-18, #13-18, #21-18, #74-18, #83-18, #87-18) of 64 screen positive T-cell clones that grew well were re-tested with three individual 15-mer peptide in the region as well as with autologous Epstein-Barr Virus-transformed B-lymphoblastoid cell line cells infected with vaccinia virus expressing E6 protein, or E7 protein, or wild type vaccinia virus Western reserve (WR). All 8 T-cell clones were positive with the E6 131-145 peptide and E6-vac (FIG. 3A-3B). As with the previous subject, a series of enzyme-linked immunospot assays were performed to determine the optimal peptide of minimal length (FIG. 3C-3E). Since none of the 9-mer peptides included in the E6 131-145 regions was positive, the enzyme-linked immunospot assay was repeated with a series of 10-mer peptides, and only SEQ ID NO. 2 (E6 133-142) was positive among the 10-mers (FIG. 3C). When two 11-mers surrounding this SEQ ID NO. 2 (E6 133-142) 10-mer and two 9-mers within it were tested, the 10-mer and the two 11-mers appeared equivalent (FIG. 3D). This was true even over a wide range of concentrations (FIG. 3E); therefore, the SEQ ID NO. 2 (E6 133-142) 10-mer peptide was designated to be the optimal peptide of minimal length.

A panel of allogeneic Epstein-Barr Virus-transformed B-lymphoblastoid cell line cells matched to one or more Human Leukocyte Antigen class I molecules of subject 18 were used in an enzyme-linked immunospot assay (clones #1-18, #4-18, #13-18, #21-18, #74-18, #80-18, #83-18, and #87-18 were tested), and allogeneic Epstein-Barr Virus-transformed B-lymphoblastoid cell line cells matched with the HLA-A68 molecule showed a positive response along with the autologous Epstein-Barr Virus-transformed B-lymphoblastoid cell line cells for all eight T-cell clones tested. To confirm this result, a chromium release assay was performed with the T-cell clones (clones #83-18 and #87-18) as effectors and Epstein-Barr Virus-transformed B-lymphoblastoid cell line cells pulsed with the E6 peptide (E6 131-145) as targets. Of the three HLA-A68 positive Epstein-Barr Virus-transformed B-lymphoblastoid cell line cells, one was known to be HLA-A6801 while another one was known to be HLA-A6802 (FIG. 3F). The results were positive for autologous Epstein-Barr Virus-transformed B-lymphoblastoid cell line cells, Epstein-Barr Virus-transformed B-lymphoblastoid cell line cells expressing A68 or A6801. Other allogeneic Epstein-Barr Virus-transformed B-lymphoblastoid cell line cells were negative including the allogeneic Epstein-Barr Virus-transformed B-lymphoblastoid cell line cells expressing the HLA-6802 molecule. Taken together, these data suggest that the restriction element of the SEQ ID NO. 2 (E6 133-142) epitope is the HLA-A6801 molecule.

Example 14

No Recognition of Homologous Peptides from Other High Risk Human Papilloma Virus by the SEQ ID NO. 1 (E6 75-83)-Specific and SEQ ID NO. 2 (E6 133-142)-Specific T-Clones To determine recognition by epitope-specific T-clone cells, the presence of homologous peptides from other high risk Human Papilloma virus types were examined. Five homologous peptides for the SEQ ID NO. 1 (E6 75-83) CD8 T-cell epitope (HPV 33, 51, 52, 56, 73), and for the SEQ ID NO. 2 (E6 133-142) epitope (HPV 31, 33, 51, 52, 58) were identified (Tables 2 and 3). These peptides were synthesized and recognition by the SEQ ID NO. 1 (E6 75-83)-specific T cell clones (#76-2 and #78-2) were examined by pulsing the peptides with autologous Epstein-Barr Virus-transformed B-lymphoblastoid cell line cells and five allogeneic Epstein-Barr Virus-transformed B-lymphoblastoid cell line cells expressing the HLA-B62 molecule.

All of the Epstein-Barr Virus-transformed B-lymphoblastoid cell line cells were recognized as measured by the number of spot forming units an enzyme-linked immunospot assay when they were pulsed with the HPV 16 E6 75-83 peptide but not with any other homologous peptides. The results were the same for the HPV 16 E6 133-142 epitope in that the Epstein-Barr Virus-transformed B-lymphoblastoid cell line cells (autologous and 5 allogeneic Epstein-Barr Virus-transformed B-lymphoblastoid cell line cells expressing the HLA-A68 molecule) were recognized only when pulsed with the SEQ ID NO. 2 (E6 133-142) peptide but not with the others (#83-18 and #87-18. These data imply that the recognition of these E6 epitopes is type-specific.

Example 15

SEQ ID NO. 1 (E6 75-83) and SEQ ID NO. 2 (E6 133-142) Specific T-Cell Clones Show the Surface Phenotype of $CD3^+CD4^-CD8^+CD16^-$ Flow cytometric analysis was used to determine the surface phenotype of SEQ ID NO. 1 (E6 75-83) and SEQ ID NO. 2 (E6 133-142) specific T-cell clones. All the tested T-cell clones (#40-2, #76-2, #78-2, #94-2 for subject 2 and #1-18, #4-18, #13-18, #21-18, #74-18, #80-18, #83-18, #87-18 for subject 18) were $CD3^+CD4^-CD8^+CD16^-$.

Example 16

Examining the Presence of Epitope-Specific Memory T-Cells by Tetramer Staining

Peripheral blood mononuclear cell samples from subject 18 collected at 4 months, 22 months, 27 months, 48 months, and 74 months (FIG. 3) after the clearance of HPV 16 infection but prior to isolation of the T-cell clones were analyzed with and without in vitro stimulation with the SEQ ID NO. 2 (E6 133-142) peptide (FIG. 3 and Table 4). Three (one in 2,146 at 4 months, one in 3,116 at 22 months, and one in 2,311 at 74 months) of the five peripheral blood mononuclear cell samples (without in vitro stimulation) demonstrated staining for the tetramer$^+$CD8$^+$ T-cells above that of the negative control (one in 5,010).

Upon stimulation with the SEQ ID NO. 2 (E6 133-142) peptide, the frequencies of these tetramer$^+$CD8$^+$ T-cells increased noticeably in the peripheral blood mononuclear cell samples taken at 4 months and 22 months (one in 512, and one in 510 respectively). Ninety eight percent and 100% of the tetramer$^+$CD8$^+$ T-cells were CD45RO$^+$ in these samples respectively. Taken together, the SEQ ID NO. 2 (E6 133-142)-specific memory T-cells were detectable at 4 months and 22 months after HPV 16 clearance.

Further, regions of the Human Papilloma virus HPV16 E6 protein, which contain multiple T cell epitopes termed "hot spots", have been identified and shown to be restricted by several Human Leukocyte Antigen Major Histocompatibility Complex I molecules. The CD8 T cell epitopes contained in these epitopes "hot spots" are relevant to 99% of the US population (Table 5).

Example 17

CD8 T-Cell Responses and Epitopes Associated with Cervical Lesion Regression

Women who were followed, but untreated for abnormal Pap smear results, were enrolled. HPV-DNA testing using the Linear Array HPV Geotyping Test (Roche Diagnostics, Indianapolis, Ind.) and enzyme-linked immunospot (ELISPOT) assay using the HPV 16 E6 and E7 antigens were performed. The subjects were categorized into three groups: regressor (n=32), persistor/progressor (n=33), or indeterminate (n=20) based on comparisons of pathological diagnoses (Pap smear or biopsy) between the last clinic visit and the current clinic visit at which blood samples were collected.

There was a higher rate of CD8 T-cell responses to the HPV 16 E6 antigen in the regressor group (17 of 32 or 53.1%) compared to the persistor/progressor group (8 of 33 or 24.2%, p=0.0225), but not for the E7 antigen (4 of 32 or 12.5% for the regressor group and 4 of 33 or 12.1% for the persistor/progressor group, p=1.0000). The results were the same when the analyses included only subjects who were HPV 16-positive (n=27, p=0.0464 for E6 and 1.0000 for E7), HPV 16-related positive (types 16, 31, 33, 35, 52, 58, and 67, n=48, p=0.0410 for E6 and 1.0000 for 37) or high-risk HPV positive (types 16, 18, 31, 33, 35, 39, 45, 51, 52, 56, 58, 59, 68, 73, and 82; n–64, p=0.0031 for E6 and 1.0000 for E7), but not low-risk HPV positive (types 6, 11, 40, 42, 43, 44, 54, 61, 70, 72, 81, and CP6108, n=19, p=1.0000 for E6 and not applicable for E7). Regions towards which immune responses were most frequently detected were E6 91-115, SEQ ID NO: 28 (n=11), E7 46-70, SEQ ID NO: 29 (n=10), and E6 46-70 SEQ ID NO: 30 (n–8) as shown in Table 6.

TABLE 6

| Epitope | Responses | Sequence | SEQ ID NO |
|---|---|---|---|
| E6 91-115 | 11 | YGTTLEQQYNKPL CDLLIRCINCQK | 29 |
| E7 46-70 | 10 | EPDRAHYNIVTFC CKCDSTLRLCVQ | 30 |
| E6 46-70 | 8 | RREVYDFAFRDLC IVYRDGNPYAVC | 31 |

CD8 T-cell immune responses to the HPV 16 E6 antigens, but not to E7 antigens are associated with SIL regression and such responses appear to be cross-reactive to other high risk HPV types. Thus, it is contemplated that HPV 16 E6 antigens are useful in the development of therapeutic vaccines for prevention and treatment of cervical cancer, such as but not limited to, increasing or enhancing regression of cervical lesions in HPV positive individuals. For example, in addition to the immunodominant epitope sequences of SEQ ID NOS: 1 and 29-31, a peptide mixture from two or more of SEQ ID NOS: 29-31 and/or from epitope sequences from HPV 16 E6 protein of SEQ ID NOS: 32-35 (Table 7) may be useful as immunogenic compositions or vaccines.

TABLE 7

| Epitope | Sequence | SEQ ID NO |
|---|---|---|
| E6 1-45 | MHQKRTAMFQDPQERPRKLPQLC TELQTTIHDIILECVYCKQQLL | 32 |
| E7 46-80 | RREVYDFAFRDLCIVYRD GNPYAVCDKCLKFYSKI | 33 |
| E6 81-115 | SEYRHYCYSLYGTTLEQQ YNKPLCDLLIRCINCQK | 34 |
| E6 116-158 | PLCPEEKQRHLDKKQRFHNIRG RWTGRCMSCCRSSRTRRETQL | 35 |

A dominant CD8 T-cell epitope was characterized from one of the subjects and was determined to be HPV16 E6 52-61 FAFRDLCIVY (SEQ ID NO: 23) restricted by the HLA-B5701 and -B5801 molecules. The utility of the HPV 16/HPV 18 E6 and E7 CD8 T-cell epitopes as the source of antigens for dendritic cell immunotherapy would be broader if the specific T-cells also recognized homolous epitopes in HPV 16 variants and other high-risk HPV types. Such homologous epitopes were tested with the use of the T-cell clones generated to define the HPV 16 E6 52-61 epitope restricted by the HLA-B5701 and -B5801 molecules.

Published sequences of HPV 16 variants and other high-risk HPV types were examined for the presence of homologous epitopes in the same region as the HPV 16 E6 CD8 T-cell epitopes. Homologous epitopes were present in 13 other high risk HPV types including HPV 18, 31, 33, 35, 39, 45, 51, 52, 56, 58, 59, 68, and 73. ELISPOT assays were performed using the HPV 16 52-61 specific T-cell clones (nos. 55 and 54/82; two T-cell clones were combined due to low cell numbers) with autologous and two allogeneic EBV-transformed B-lymphoblastoid cell line (B-LCL) expressing the HLA-B5801 molecule, pulsed with these peptides. For clone no. 55, positive responses were seen for peptides HPV 16 52-61, HPV 35 45-54, HPV 45 47-56, and HPV 73 45-54. Larger number of peptides demonstrated positive responses for clone no. 54/82 including HPV 16 52-61, HPV 31 45-54, HPV33 45-54, HPV 35 45-54, HPV 39 47-56 HPV 45 47-56, HPV 51 45-54, HPV 58 45-54, and HPV 73 45-54. These results suggest that recognition of these T-cell epitopes are cross-reactive with homologous epitopes of many other high risk HPV types.

Example 18

CANDIN (Allermed, San Diego, Calif.) as a HPV Vaccine Adjuvant

Human papillomavirus type 16 (HPV 16) E6 46-80 (35-mer, SEQ ID No: 33, $CH_3$—) peptide was used as a model antigen since it is known to contain the dominant CD8 T-cell epitope in the C57/BL6 background. SEQ ID No: 33 is acetylated ($CH_3$—) at the amino terminus and amidated at the carboxyl ternius (—$NH_2$) to enhance stability. The effect of CANDIN as adjuvant on enhancing immune responses was assessed by vaccinating C57BL/6 mice with the HPV 16 E6 46-80 peptide.

It is well known in the art that the HPV-16 E6 protein contains CD8 and CD4 epitopes. The advantages of using synthetic peptides as vaccine are numerous, however available adjuvants for peptide vaccines are limited. The only widely used adjuvant for peptide vaccine is an aluminum-based adjuvant that is known to elicit predominantly a Th2 immune response, which is ineffective at producing CD8 T-cells (40). Therefore, the aluminum-based adjuvant would not be useful for a vaccine designed to stimulate T-cell responses, such as instant HPV peptide vaccine. CANDIN (Allermed, San Diego, Calif.), a whole cell extract of *Candida albicans* approved by FDA for skin testing of tuberculosis, was selected as adjuvant for HPV E6 peptides vaccines.

Figure 5C:
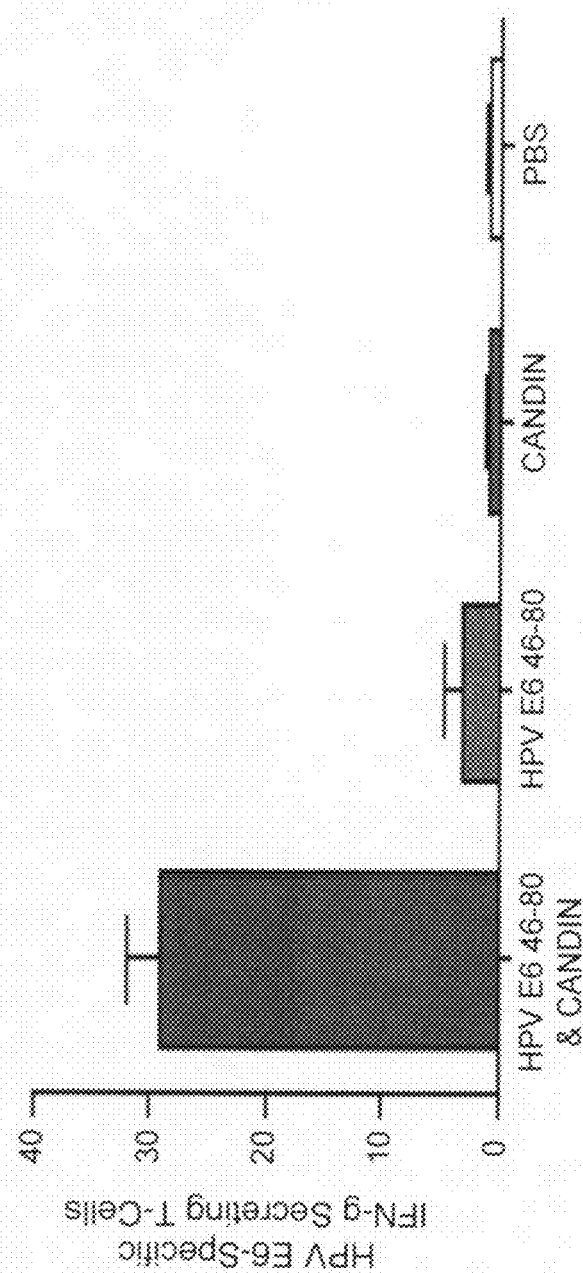

Initially, a dose range-finding study was performed in which mice (n=2 per group) were vaccinated intradermally once a week for three weeks with one of the six different combinations of peptide and CANDIN (1 ug/100 ul, 10 ug/100 ul, 100 ug/100 ul, 2 ug/200 ul, 20 ug/200 ul, or 200 ug/200 ul). Mice were sacrificed one week after the last injection, and intracellular cytokine staining was performed. The spleen cells were incubated overnight in the presence or absence of HPV 16 E6 48-57 (SEQ ID No: 36, 10-mer, EVYDFAFRDL), E6 46-60 (SEQ ID No: 37, 15-mer, RREVYDFAFRDLCIV), or E6 46-80 (SEQ ID No: 33, 35-mer, $CH_3$—) peptide. Spleen cells were labeled (IFN-g FITC and CD8 PE), and $3 \times 10^5$ events were acquired. The number of IFN-gamma expressing antigen-specific T-cells were compared among groups. The greatest number of antigen-specific T-cells were found in mice vaccinated with the 20 ug/200 ul combination, followed closely by mice injected with 200 ug/200 ul (data not shown). Such results suggested that the amount of adjuvant (CANDIN), rather than the amount of antigen (HPV E6 peptides), has a more significant effect in enhancing immune responses. The vaccinations were repeated using the 20 ug/200 ul combination (3 intradermal injections 4 days, 1 week, 2 weeks, or 3 weeks apart). Intracellular cytokine staining results for spleen cells among mice injected with the "peptide with CANDIN" (n=5), "peptide alone" (n=5), "CANDIN alone" (n=5), and the "PBS control" (n=5) groups were compared and shown in FIGS. 5A-5C. FIG. 5A shows the results obtained using HPV 16 E6 48-57 (SEQ ID No: 36, 10-mer, EVYDFAFRDL) as antigen. FIG. 5B shows the results obtained using HPV 16 E6 46-60 (SEQ ID No: 37, 15-mer, RREVYDFAFRDLCIV) as antigen. FIG. 5C shows the results obtained using HPV 16 E6 46-80 (SEQ ID No: 33, 35-mer, $CH_3$—) as antigen. SEQ ID No: 33 is acetylated ($CH_3$—) at the amino terminus and amidated at the carboxyl ternius (—$NH_2$) to enhance stability.

Figure 6A:
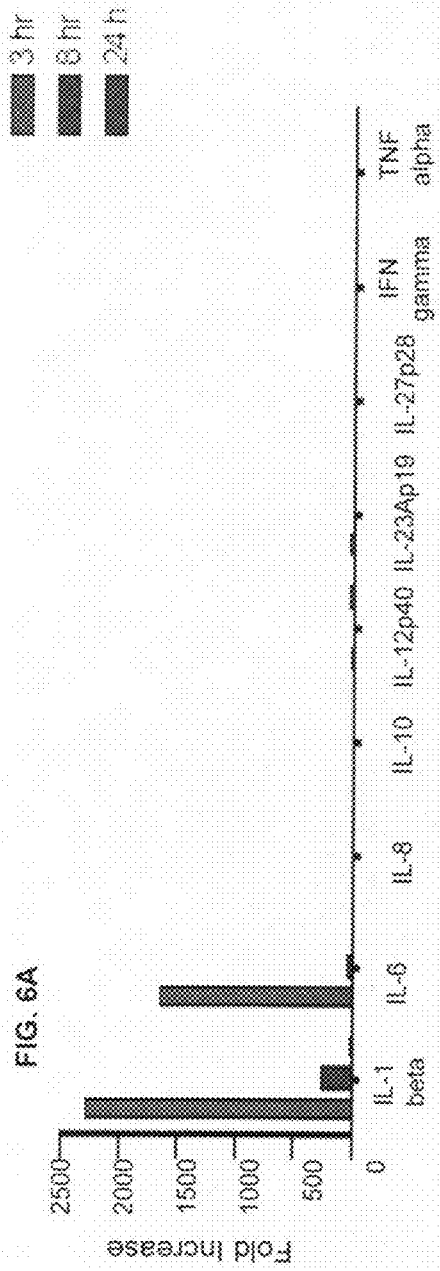
FIGS. 6A-6B show quantitative RT-PCR analysis of monocyte-derived Langerhan cells treated with CANDIN (Allermed, San Diego, Calif.). Langerhan cells treated with *E. coli* LPS were used as positive control (FIG. 6A) and Langerhan cells treated with CANDIN revealed the expression of IL-12p40 consistently (FIG. 6B). The experiment was performed three times.
Figure 6B:
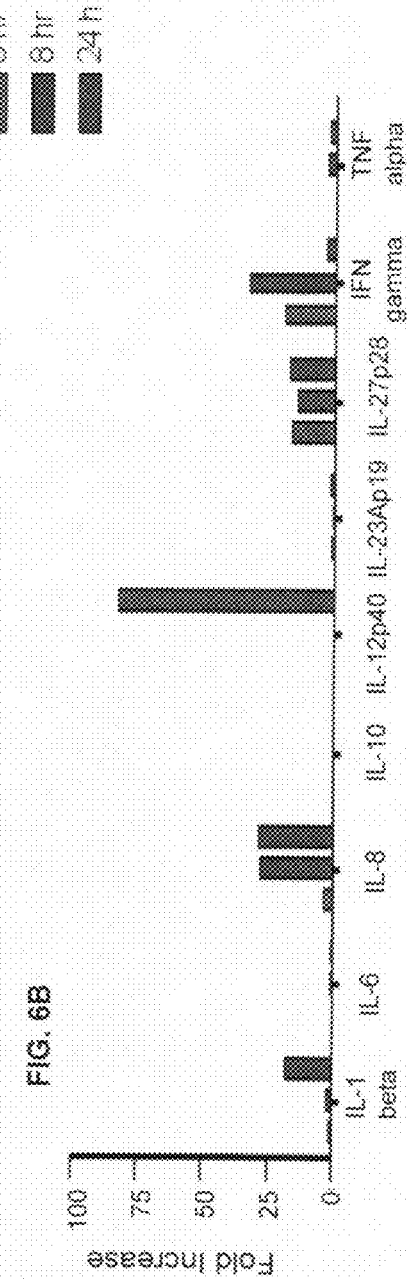

Quantitative RT-PCR Analysis of Monocyte-Derived Human Langerhan Cells Treated with CANDIN Since Langerhan cells are likely to be the antigen presenting cells in the skin, expression of various cytokines (IL-1 beta, IL-6, IL-9, IL-10, IL-12p40, IL-23Ap19, IL-27p28, IFN-gamma, and TNF-alpha) was examined in monocyte-derived Langerhan cells stimulated by CANDIN using qRT-PCR. Monocytes from PBMCs taken from a healthy donor were negatively selected (Monocyte Isolation Kit II, Miltenyi Biotec, Auburn, Calif.) and were treated with GM-CSF, IL-4, and TGF-b1 for 7 days as described by Fahey and colleagues. Successful conversion to a Langerhan cell phenotype was demonstrated by the expression of CD1a, Langrin, and E-cadherin using FACS analysis. One million Langerhan cells each were treated with 50 ul/ml or 150 ul/ml of CANDIN, along with E. coli LPS as a positive control and media only as a negative control. Cells were harvested at 3, 8, and 24 hr for RNA extraction, and qRT-PCR analysis was performed in duplicate for IL-1 beta, IL-6, IL-8, IL-10, IL-12p40, IL-23Ap19, IL-27p28, IFN-gamma, and TNF-alpha. The threshold cycles were normalized to human glyceraldehyde 3-phosphate dehydrogenase (GAPDH) expression as FIGS. 6A-6B. Langerhan cells treated with E. coli LPS were used as positive control (FIG. 6A) and Langerhan cells treated with CANDIN revealed the expression of IL-12p40 consistently (FIG. 6B).

ELISA Assay for IL-12P40 Protein

Figure 7:
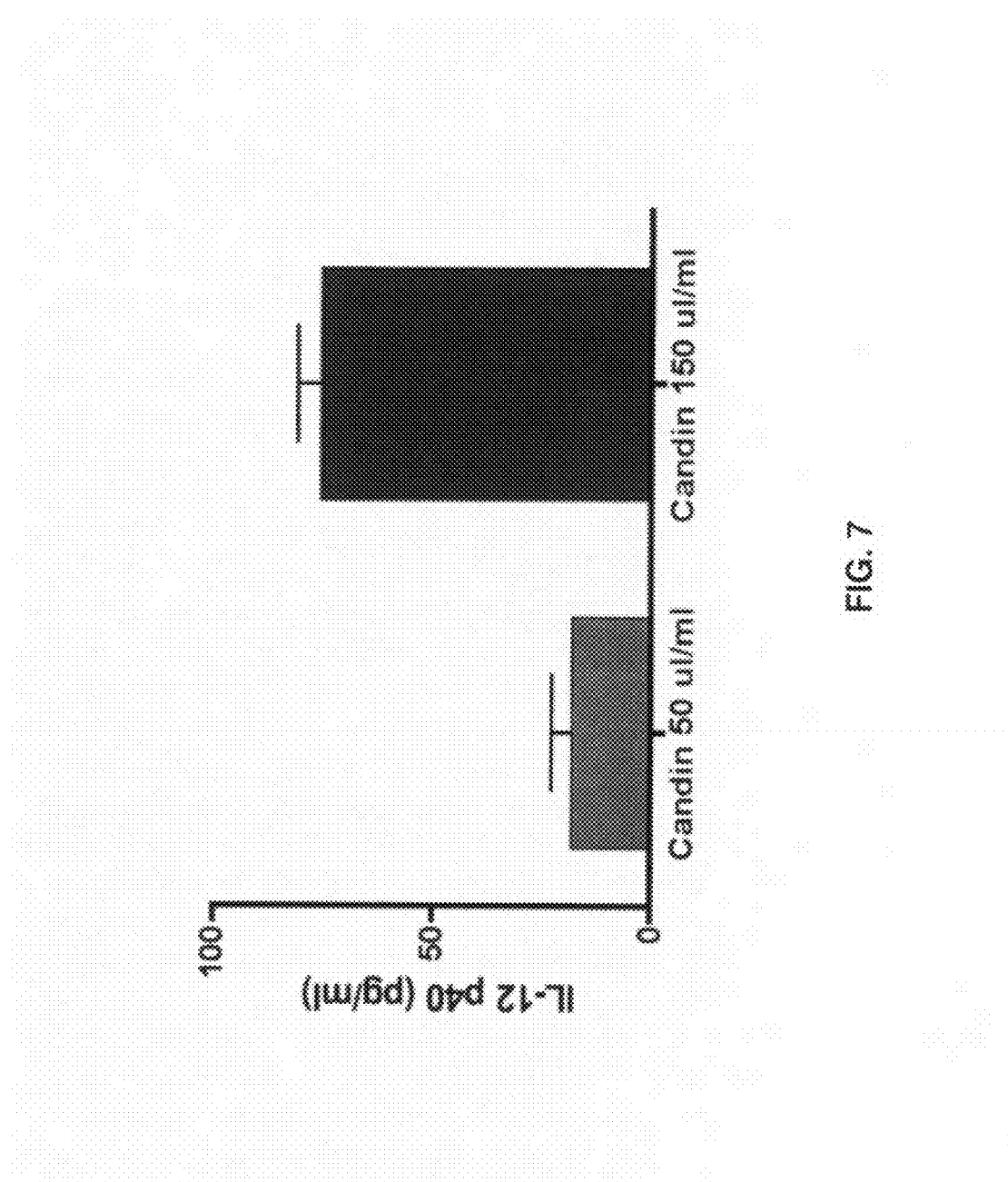
FIG. 7 shows ELISA results of supernatants of Langerhan cells treated with CANDIN (Allermed, San Diego, Calif.). Supernatants from the above experiment were analyzed for the IL-12p40 protein expression. The results from the 24 hour time point are shown.

Supernatants (50 ul) from the above experiments were analyzed for the presence of IL-12p40 protein using the OptEIA™ kit (BD, Franklin Lakes, N.J.) according to the manufacturer's instructions. FIG. 7 shows ELISA results of supernatants of Langerhan cells treated with CANDIN (Allermed, San Diego, Calif.). Supernatants from the experiment shown in FIG. 6 were analyzed for the IL-12p40 protein expression.

Example 19

CD4 Positive T Cell Reponses to HPV-16 E6 and E7

CD8+ T-cell immune responses against the HPV-16 E6 protein but not the E7 protein were significantly associated with a favorable clinical trend in subjects being followed for cervical abnormalities (41). The role of CD4+ T-cell responses to the HPV-16 E6 and E7 proteins was examined in the outcomes of subjects being studied for abnormal Papanicolaouu (Pap) smear results. Subjects with a recent history of abnormal Papanicolaouu smear were eligible, and colposcopy guided biopsy was performed at enrollment. Interferon-γ enzyme-linked immunospot assay, and fluorescent activated cell sorter analysis were performed. Subjects with histological diagnoses of cervical intraepithelial neoplasia 1, 2, or 3 were considered to have short-term persistence of cervical abnormality and were called "persistors" (n=51) while those of normal histology were designated to be "regressors" (n=33). For the CD4+ T-cell responses, not only were the responses to E6 overall (Table 8) associated with a favorable clinical outcome, but also to a number of regions within the E6 protein. Furthermore, the regressors were more likely to have 2 or more E6-positive or E7-positive peptide regions as compared to the persistors (p=0.0035 or p=0.042 respectively) (Table 9). A significantly higher percentage CD4+ T-cell response was detected in the regressors (15/33 or 45.5%) compared to the persistors (10/51 or 19.6%) (p=0.015) for the E6 peptides but not for the E7 peptides. The CD4+ responses to certain E6 regions [E6 (16-40), E6 (91-115), E6 (106-130), and E6 (136-158)] were also significantly higher in the regressors. These data suggested that CD4+ and CD8+ T-cell responses to the HPV-16 E6 protein are associated with a favorable clinical trend.

HPV-DNA Typing

HPV-DNA typing was performed on THINPREP specimens collected on the day of enrollment from all 88 subjects. Overall, at least 1 type of HPV-DNA was detected in 83 (95.4%) of 87 subjects. HPV-16 was the most commonly detected type (n=22, 25.3%) followed by HPV-39 (n=17, 19.5%), HPV-54 (n=15, 17.2%), HPV-51 (n=14, 16.1%), and HPV-35 (n=13, 14.9%). In regard to the number of HPV types detected, 28 (32.2%) of 87 subjects had a single detectable HPV type; 2 HPV types were detected in 14 (16.1%) subjects; 3 HPV types in 14 (16.1%) subjects; and 4 or more types in 27 (31.0%) subjects. Fifty subjects (57.5%) were positive for at least 1 HPV-16-related types, and 72 (82.8%) for high-risk HPV types.

CD4+ T-Cell Responses to HPV-16 E6 and E7

The CD4+ T-cell responses to HPV-16 E6 peptides were significantly higher in the regressors (15/33 or 45.5%) compared with the persistors (10/51 or 19.6%) (p=0.015). Although the percentage in the CD4+ T-cell responses to HPV-16 E7 antigens was also higher in the regressor group (5/33 or 15.2%) compared to the persistor group (3/51 or 5.9%), the difference was not statistically significant (p=0.25). Additional comparisons were made for subgroups of subjects based on HPV-DNA detected (Table 8).

TABLE 8

Table 8. HPV-16 E6- or E7-specific IFN-γ ELISPOT assay results based on clinical trend.

| Stratification by HPV types | Regressors | Persistors | p | Regressors | Persistors | p |
|---|---|---|---|---|---|---|
| | E6-positive, no. (%) | | | E7-positive, no. (%) | | |
| All | 15/33 (45) | 10/51 (20) | .015 | 5/33 (15) | 3/51 (6) | .25 |
| High-risk HPV | 8/22 (36) | 9/46 (20) | .15 | 2/22 (9) | 3/46 (7) | .66 |
| HPV-16-related | 6/18 (33) | 5/30 (17) | .29 | 2/18 (11) | 1/30 (3) | .55 |
| HPV-16 | 3/10 (30) | 3/11 (27) | .64 | 0/10 (0) | 1/11 (9) | 1.0 |

Further comparisons were made for each of the ten E6 regions or six E7 regions. The comparisons reached statistical significance for the following regions between the regressors and the persistors: E6 (16-40) (24% vs. 2%, p=0.0020), E6 (31-55) (21% vs. 6%, p=0.044), E6 (61-85) (12% vs. 0%, p=0.021), and E6 (91-115) (18% vs. 2%, p=0.013). Among the subjects who were high-risk HPV-positive, the comparisons reached statistical significance for the following regions: E6 (1-25) (18% vs. 2%, p=0.035), E6 (16-40) (23% vs. 2%, p=0.012), E6 (61-85) (14% vs. 0%, p=0.031), E6 (91-115) (23% vs. 2%, p=0.012), E6 (106-130) (27% vs. 4%, p=0.012), and E6 (136-158) (18% vs. 2%, p=0.035). Among subjects who were positive for HPV-16 related types, the comparisons were significant for E6 (1-25)(17% vs. 0%, p=0.047), E6 (16-40)(22% vs. 0%, p=0.016), E6 (61-85) (17% vs. 0%, p=0.047), E6 (91-115)(22% vs. 0%, p=0.016), E6 (106-130)(28% vs. 3%, p=0.023), and E6 (136-158)(17% vs. 0%, p=0.047).

Overall, 27 (32.1%) of 84 subjects demonstrated at least 1 positive peptide region within E6 and/or E7. Fourteen subjects (16.7%) were positive for 1 region; 3 subjects (3.6%) for 2 regions; 2 subjects (2.4%) for 3 regions; 3 subjects (3.6%) for 4 regions; 1 subject (1.2%) for 6 regions; 1 subject (1.2%) for 7 regions; 1 subject (1.2%) for 8 regions; 1 subject (1.2%) for 10 regions; and 1 subject (1.2%) for 12 regions. Additionally, the numbers of positive peptide regions within E6 or E7 were compared, and the regressors were more likely to have 2 or more E6-positive (p=0.0035) or E7-positive (p=0.042) peptide regions as compared to the persistors (Table 9).

TABLE 9

Comparison between regressors and persistors in the number of positive CD4+ T-cell peptide region(s) in E6 or E7.

| | Number of positive peptide region(s) | | | |
|---|---|---|---|---|
| | 0 | 1 | ≥2 | Total |
| E6-positive | | | | |
| Regressor, no. | 18 | 5 | 10 | 33 |
| Persistor, no. | 41 | 8 | 2 | 51 |
| Total | 59 | 13 | 12 | 84 |
| E7-positive | | | | |
| Regressor, no. | 28 | 1 | 4 | 33 |
| Persistor, no. | 48 | 3 | 0 | 51 |
| Total | 76 | 4 | 4 | 84 |

To examine whether the positive CD4+ T-cell responses to HPV-16 E6 and E7 peptides may be attributed to cross-reactivity to other HPV types, HPV-16 infected subjects were removed in the analysis of CD4+ T-cell responses (non-HPV-16-positive subjects). Overall, positive CD4+ T-cell responses were detected against the HPV-16 E6 protein (20/63 or 31.7%) or the E7 protein (7/63 or 11.1%) in subjects without detectable HPV-16 infection. When the results were evaluated based on clinical trends, the CD4+ T-cell responses to the HPV-16 E6 peptides were detected in 12 of 23 regressors and 8 of 40 persistors (52.2% vs. 20.0%, p=0.012). The responses to the HPV-16 E7 peptides were positive in 5 of 23 regressors and 2 of 40 persistors (21.7% vs. 5.0%, p=0.089). In the non-HPV-16-positive group, positive CD4+ T-cell responses were detected against both HPV-16 E6 and E7. Moreover, a favorable clinical outcome remained significantly associated with positive responses to regions within the HPV-16 E6 protein. Since the sequences of these peptides were based on HPV-16, positive responses detected in the subjects with non-HPV-16 HPV types may be due either to memory HPV-16 E6-specific T-cells from previous HPV-16 infection or to cross-recognition of HPV-16 E6 peptides by CD4+ T-cells specific for homologous peptides of other HPV types.

Example 20

Dosage and Toxicity of the HPV Vaccine Containing E6 Peptides and CANDIN

Although CANDIN (Allermed, San Diego, Calif.) antigen is FDA-approved for human use, the HPV peptide-CANDIN combination has never been tested. The safety of the HPV peptide-CANDIN combination is examined in mice by a multiple-dose toxicity study (GLP) to examine the doses equivalent to the two highest human doses (250 and 500 micrograms per peptide). To examine whether CANDIN adjuvant enhances T-cell immunity to an HPV antigen, IFN-g ELISPOT assays is performed and the results of mice injected with peptides alone with those of mice injected with peptides and adjuvant at the same dose are compared.

Because the CD4 and CD8 T-cell responses to HPV-16 E6 protein are significantly associated with cervical lesion regression (42, 44), the vaccine consists of four HPV-16 E6 peptides, all of which are acetylated ($CH_3$—) at the amino terminus and amidated at the carboxyl ternius (—$NH_2$) to enhance stability: E6 1-45 (SEQ ID No: 32, $CH_3$-MHQKRTAMFQDPQERPRKLPQLCTELQT-TIHDIILECVYCKQQLL-$NH_2$), E6 46-80 (SEQ ID No: 33, $CH_3$-RREVYDFAFRDLCIVYRDGNPYAVCDK-CLKFYSKI-$NH_2$), E6 81-115 (SEQ ID No: 34, $CH_3$-SEY-RHYCYSLYGTTLEQQYNKPLCDLLIRCINCQK-$NH_2$), and E6 116-158 (SEQ ID No: 35, $CH_3$-PLCPEEKQRHLD-KKQRFHNIRGRWTGRCMSCCRSSRTRRETQL-$NH_2$).

Commercially produced cGMP-grade peptides (90% purity; CPC Scientific, San Jose, Calif.) is examined. Their safety for human use is ensured, in accordance with FDA requirements, by testing 14-day sterility (USP <71>), testing pyrogens, describing appearance and identity, analyzing amino acids, determining impurities by HPLC, assessing $H_2O$ content and net active peptide, and describing any organic solvents (each peptide to be assessed individually as per the FDA). The lyophilized peptide mixture is dissolved using one drop (~20 µL) of sterile, pyrogen-free, endotoxin-free, and mycoplasma-free dimethylsulfoxide (DMSO; WAK-Chemie Medical GMBH, Steinbach, Germany), and then 300 µL) of CANDIN (dose used for treating skin warts) will be added. The mixture is vortexed lightly prior to inoculation.

Four administrations 3 weeks apart are planned for the Phase I trial; therefore, five administrations in the animal study are performed (days 1, 8, 15, 22, and 29). The dorsal side of each animal is divided into five areas, and each area is sequentially injected. To enhance immune responses, intradermal administration is used, which places the antigens proximal to Langerhans cells, the antigen-presenting cells in skin.

The immunodominant HPV-16 E6 CD8 T-cell epitope has been shown to be E6 48-57, presented by the H-2K$^b$ molecule (43). The T-cell response to this epitope is examined using intracellular cytokine staining of IFN-g, using spleen cells from five mice each from Groups 3-6 (spleens from the other five mice will be used for histology) that are sacrificed on days 32 and 60. Phorbol myristate acetate and ionomycin are used as a positive control, medium is used as a negative control for IFN-g secretion, and a pool of peptides included in the vaccine will also be tested for IFN-g secretion. The number of HPV-specific T-cells (# spot-forming units in antigen wells minus # spot-forming units in medium-only wells) is compared between Groups 3 and 5 as well as Groups 4 and 6. Statistical significance is examined using ANOVA analysis, and mice in 'core' and 'recovery' groups will be analyzed separately.

TABLE 10

Six groups to be examined in the multiple-dose toxicology study

| Group | Treatment | Antigen(s) Dose (μg/ peptide) | Adjuvant Dose (μL) | Number of Animals | |
|---|---|---|---|---|---|
| | | | | Day 32 Core* | Day 60 Recovery† |
| 1 | Saline control | 0 | 0 | 10 F | 10 F |
| 2 | Adjuvant alone | 0 | 300 | 10 F | 10 F |
| 3 | Antigens alone | 250 | 0 | 10 F | 10 F |
| 4 | Antigens alone | 500 | 0 | 10 F | 10 F |
| 5 | Antigens + Adjuvant | 250 | 300 | 10 F | 10 F |
| 6 | Antigens + Adjuvant | 500 | 300 | 10 F | 10 F |

*Core, to be sacrificed 3 days after injection.
†Recovery, to be sacrificed 4 weeks after the last injection.
F, female.

Example 21

Figure 8:
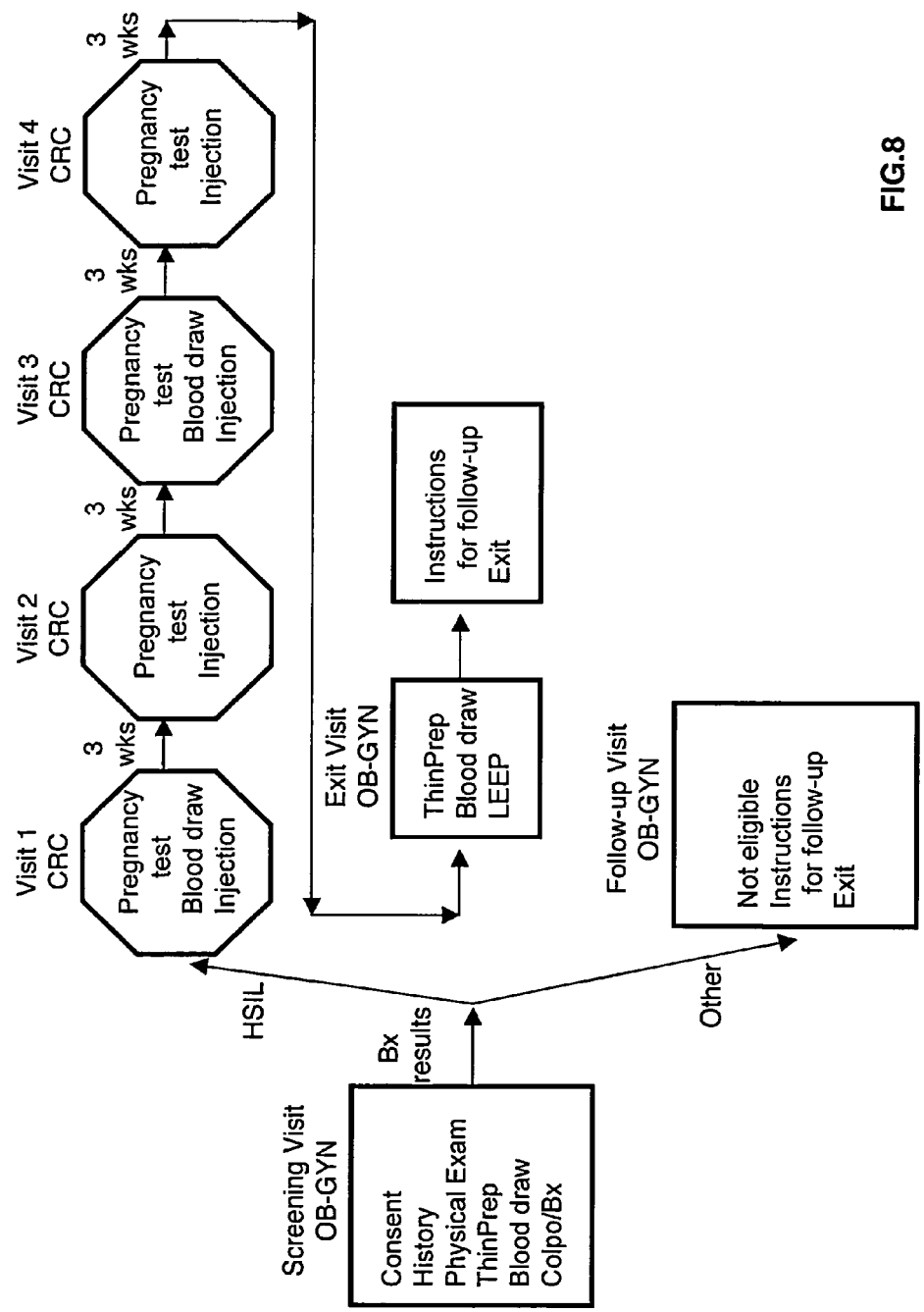
FIG. 8 shows diagram of a vaccination scheme. Each subject receives all the injections at the same dose. CRC, clinical Research Center; Colpo, colposcopy; Bx, biopsy.

Phase I Clinical Trial of a HPV Therapeutic Vaccine Containing E6 Peptides and CANDIN in Women with Biopsy-Proven High-Grade Squamous Intraepithelial Lesion A single-arm, open-label, dose-escalation Phase I clinical trial of a HPV therapeutic vaccine containing E6 peptides and CANDIN in women with biopsy-proven high-grade squamous intraepithelial lesions (HSIL) is performed. The vaccine consists of HPV peptides and CANDIN. The vaccine consists of four HPV-16 E6 peptides, all of which are acetylated ($CH_3$—) at the amino terminus and amidated at the carboxyl ternius (—$NH_2$) to enhance stability: E6 1-45 (SEQ ID No: 32, $CH_3$-MHQKRTAMFQDPQER-PRKLPQLCTELQTTIHDIILECVYCKQQLL-$NH_2$), E6 46-80 (SEQ ID No: 33, $CH_3$-RREVYDFAFRDL-CIVYRDGNPYAVCDKCLKFYSKI-$NH_2$), E6 81-115 (SEQ ID No: 34, $CH_3$-SEYRHYCYSLYGTTLEQQYNK-PLCDLLIRCINCQK-$NH_2$), and E6 116-158 (SEQ ID No: 35, $CH_3$-PLCPEEKQRHLDKKQRFHNIRGRWTGRC-MSCCRSSRTRRETQL-$NH_2$) Vaccine recipients are women with untreated biopsy-proven HSILs. Four injections (one every 3 weeks) of the vaccine are intradermally administered in upper extremities. Blood is drawn for CD3 ELISPOT (to assess CD4 and CD8 responses) and immune suppressor cell analysis before and after the second and fourth injections. Clinical response is assessed by performing LEEP excision after four injections. HPV-DNA testing is performed before and after four injections (FIG. 8). Each subject is given a single dose level for all four injections. The first cohort of six subjects receives a 50 μg dose; when the cohort is completed, the next subject receives the next higher dose level (detailed below and in FIG. 9). After all doses are tested (assuming no dose-limiting toxicity was observed), maximum tolerated dose (MTD), immunologically optimal dose (IOD), and clinically optimal dose (COD) are determined. An additional 30 subjects are vaccinated at the final dose (see below).

Figure 9:
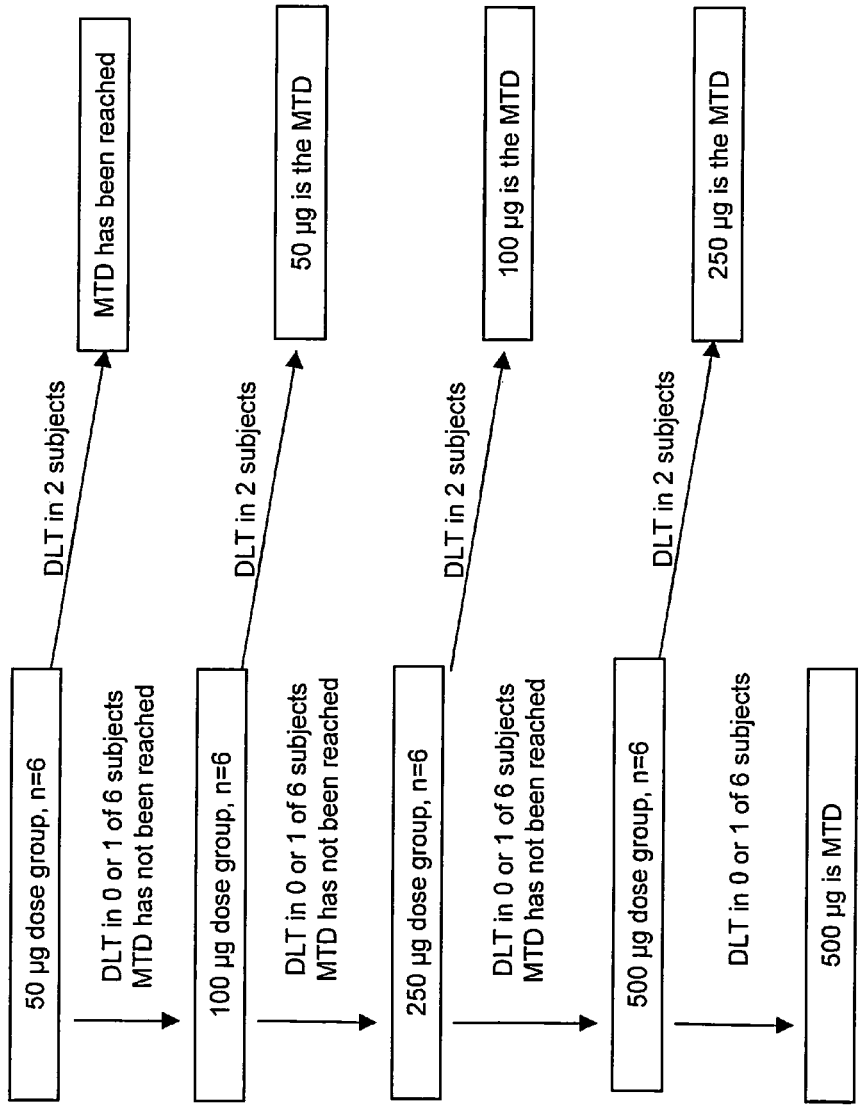
FIG. 9 shows dose-escalation plan of vaccination. A total of 24 subjects are enrolled in the dose-escalation phase, and an additional 30 subjects are recruited at the final dose.

The first six subjects each receive the lowest dose (50 micrograms) of peptide as long as dose-limiting toxicity is not seen in more than one recipient. The first two subjects in each dose level are staggered by at least one week as per FDA recommendations. The dose level is increased as shown in FIG. 9 until maximum tolerated dose is reached or the study is completed. Thirty additional subjects are vaccinated at the final dose for further assessment of clinical response.

THINPREP samples are tested for 37 HPV genotypes using the "Linear Array HPV Genotyping Test" according to the manufacturer's instructions (Roche Molecular Diagnostics, Inc., Alameda, Calif.). The HPV types to be tested include 6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73, 81, 82, 83, 84, IS39, and CP6108. The human b-globin signal is be assayed as a positive control for sample adequacy for DNA content from each sample. Positive-control samples (with added HPV plasmid DNA and plasmid-encoded human b-globin gene) and negative-control samples (no HPV plasmid DNA and no human b-globin gene) are provided by the manufacturer and are included in each experiment.

After each blood draw, PBMCs are separated into $CD14^+$ and $CD14^-$ populations and cryopreserved. To eliminate interassay variability, all three blood samples (before vaccination, after two vaccinations, and after four vaccinations) are used to establish T-cell lines and to perform ELISPOT assays. CD3 T-cell lines are established by stimulating in vitro magnetically selected CD3 cells with autologous mature dendritic cells exposed to HPV 16 E6-vac, E7-vac, E6-GST, and E7-GST. ELISPOT assays are performed as described (45). 16 regions within the HPV-16 E6 and E7 proteins (E6 1-25, E6 16-40, E6 31-55, E6 46-70, E6 61-85, E6 76-100, E6 91-115, E6 106-130, E6 121-145, E6 136-158, E7 1-25, E7 16-40, E7 31-55, E7 46-70, E7 61-85, and E7 76-98) are examined. The assay is performed in triplicate. In order to compare each region before vaccination and after 2 or 4 injections, a t test for paired samples is performed, as described previously (46). Therefore, each subject is assessed in terms of the number of regions with statistically significant increased T-cell responses after two injections or four injections.

To measure circulating Treg cells and Myeloid-derived suppressor cells (MDSC), a small amount of PBMCs ($2\times10^6$ cells) from each blood draw are used to monitor levels of circulating Tregs and MDSC to assess whether vaccination may inadvertently stimulate them (47). The number of $CD4^+$ $CD25^+$ forkhead box (FOX) $P3^+$ cytotoxic T lymphocyte-associated antigen-4 $(CTLA-4)^+$ cells are determined by flow cytometry using anti-human FoxP3 staining kit (allophycocyanin, eBiosciences, San Diego, Calif.), CTLA-4 peridininchlorophyll-protein complex (BD PharMingen, San Jose, Calif.), CD25 phycoerythrin, and CD4 fluorescein isothiocyanate (BD Biosciences, San Jose, Calif.) (48). Cells are analyzed by flow cytometry (XL-MCL, Beckman Coulter Inc., Fullerton, Calif.). The percent of circulating Treg cells (% $CD4^+CD25^+FoxP3^+CTLA-4^+$/total $CD4^+$) is determined before vaccination, after two, and after four injections. The Treg cells are considered to have increased if after two or four injections, the percent is at least two-fold greater than before injections. To enumerate MDSC, PBMCs are stained with CD14 and HLA-DR antibodies, and the percentage of CD14+ HLA-$DR^{-/low}$ are assessed (49). Representative sections of LEEP specimens are used for immunohistochemical staining using FOXP3 (rabbit polyclonal; Abcam, Cambridge, Mass.) to innumerate the number of cervical Tregs (50). The densities of FOXP3+ cells are determined using an image analysis software, and only cells with nuclear staining are counted.

The following references were cited herein:
1. World Health Organization, (1990) Global Estimates for Health Situationa Assessment and Projections 29-30.
2. Parkin et al. (1999) Intl J Cancer 80:827-841.
3. Silverberg and Lubera, (1988) Cancer Journal for Clinicians 38:5-22.
4. Walboomers, J. M. et al. (1999) J Pathol 189:12-19.
5. zur Hausen, H. (1996) Biochim Biophys Acta 1288:F55-78.
6. Munoz et al. (2003) N Engl J Med 348(6):518-527.
7. Beaudenon et al. (1986) Nature 321(6067):246-249.
8. Crum et al. (1985) J Virol 54(3):675-681.
9. Reid et al. (1987) Obstet Gynecol Clin North Am 14(2): 407-429.
10. Lorincz et al. (1986) J Virol 58:225-229.
11. Lorincz et al. (1987) Virol 159:187-190.
12. Fuchs et al. (1988) Int J Cancer 41(1):41-45.
13. Koutsky et al. (1992) N Engl J Med 327(18):1272-1278.
14. Richart et al. (1969) Am J Obstet Gynecol 105:383-393.
15. Nash et al. (1987) Obstet Gynecol 69:160-162.
16. Campion et al. (1986) Lancet 2:236-240.
17. zur Hausen, H. (1999) Semin Cancer Biol 9:405-411.
18. Greenberg, P. D. (1991) Adv Immunol 49:281-355.
19. Ossendorp et al. (1998) J Exp Med 187:693-702.
20. Romerdahl et al. (1988) Cancer Res 48:2325-2328.
21. Schild et al. (1987) Eur J Immunol 17:1863-1866.
22. Bontkes et al. (1997) Br J Cancer 76 (10):1353-1360.
23. Toes et al. (1999) J Exp Med 189:753-756.
24. Bennett, S. R. et al. (1998) Nature 393:478-480.
25. Ridge, J. P. et al. (1998) Nature 393:474-478.
26. Schoenberger et al. (1998) Nature 393:480-483.
27. Snijders et al. (1998) Int Immunol 10:1593-1598.
28. Bourgault et al. (2000) Eur J Immunol 30:2281-2289.
29. Alexander, M. et al. (1996) Am J Obstet Gynecol 175: 1586-1593.
30. Evans, E. M. et al. (1997) Cancer Res 57:2943-2950.
31. Nakagawa, M. et al. (2000) J Infect Dis 182:595-598.
32. Yoon, H. et al. (1998) Virus Res 54(1):23-29.
33. Kaech, S. M, et al. (2002) Nat Rev Immunol 2:251-62.
34. Romani, N. et al. (1996) J Immunol Methods 196:137-151.
35. Osada, T. et al. (2006) Int Rev Immunol 25:377-413.
36. Ting and Manos, In: Innis, et al, eds. Polymerase Chain Reaction Protocols: A Guide To Methods and Applications. San Diego, Calif.: Academic Press 1990.
37. Nakagawa et al. (2004) Clinical and Diagnostic Lab. Immunology 11:889-896.
38. Walls, E. V. and Crawford L H, In: Klaus G G B, ed. Lymphocytes: A Practical Approach. Oxford, U.K.: IRL Press, 1987
39. Nakagawa et al. (1997) J Infect Dis 175:927-931.
40. Gupta R K. Adv Drug Deliv Rev. 1998; 32:155-172.
41. Nakagawa M et al. J Low Genit Tract Dis. 2010; 14:124-9.
42. Kim K H et al. Cancer Immun 6:9.
43. Peng S et al. J. Virol. 2004; 78:8468-76.
44. Kim K H et al. Submitted.
45. Nakagawa M et al. Clin Diagn Lab Immunol. 2005; 12:1003-5.
46. Kim K H et al. Clin Vaccine Immunol. 2007; 14:362-8.
47. Banerjee D K et al. Blood. 2006; 108:2655-61.
48. Molling J W et al. International Journal of Cancer. 2007; 121:1749-55.
49. Hoechst B et al. Gastroenterology. 2008; 135:234-43.
50. Kobayashi A et al. Mucosal Immunology. 2008; 1:412-20.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of decreasing infection from human papilloma virus in an individual, comprising:
    administering to the individual an immunologically effective amount of an immunogenic composition comprising a synthetic peptide comprising SEQ ID NO: 32, a synthetic peptide comprising SEQ ID NO: 33, a synthetic peptide comprising SEQ ID NO: 34, and a synthetic peptide comprising SEQ ID NO: 35; wherein said composition activates a specific immune response in the individual, thereby decreasing infection from human papilloma virus in the individual and wherein each synthetic peptide does not comprise full-length HPV E6 protein.

2. The method of claim 1, wherein said synthetic peptides are acetylated at the amino terminus, amidated at the carboxyl terminus or acetylated at the amino terminus and amidated at the carboxyl terminus.

3. A method for increasing regression of Human Papilloma Virus (HPV)-associated cervical lesions in an HPV positive individual, comprising
    administering an immunogenic composition comprising peptides derived from immunodominant epitopes of HPV E6 protein effective to generate CD8 T-cell responses specific against the HPV,
    wherein the composition comprises peptides consisting of SEQ ID NO:32, SEQ ID NO:33, SEQ ID NO:34, and SEQ ID NO:35.

4. The method of claim 3, wherein said peptides are synthetic peptides acetylated at the amino terminus, amidated at the carboxyl terminus or acetylated at the amino terminus and amidated at the carboxyl terminus.

5. The method of claim 3, wherein the immunogenic composition further comprises an adjuvant.

6. The method of claim 5, wherein said adjuvant comprises antigens from *Candida albicans*, mumps virus, or *Trichophyton*.

7. The method of claim 6, wherein said adjuvant is concentrated whole cell extract made from lyophilized cells of *Candida albicans*.

8. The method of claim 7, wherein said adjuvant is contained in said composition in an antigen/adjuvant ratio of about 20 micrograms antigen per 200 microliter of adjuvant to about 20 micrograms antigen per 500 microliter of adjuvant.

9. The method of claim 8, wherein said immunogenic composition is administered intradermally.

10. The method of claim 1 wherein the immunogenic composition further comprises an adjuvant, wherein immunization of mice with the immunogenic composition comprising the adjuvant enhances stimulation of interferon-gamma-expressing HPV-antigen-specific T cells as compared to immunization of mice with the immunogenic composition lacking the adjuvant.

11. The method of claim 4 wherein the peptides consisting of SEQ ID NO:32, SEQ ID NO:33, SEQ ID NO:34, and SEQ ID NO:35 are each acetylated at the amino terminus and amidated at the carboxyl terminus.

12. The method of claim 11 wherein the composition further comprises an adjuvant, wherein said adjuvant comprises antigens from *Candida albicans*, mumps virus, or *Trichophyton*.

13. The method of claim 12 wherein the adjuvant comprises whole cell *Candida albicans* extract.

14. The method of claim 3 wherein the immunogenic composition further comprises an adjuvant, wherein immunization of mice with the immunogenic composition comprising the adjuvant enhances stimulation of interferon-gamma-expressing HPV-antigen-specific T cells as compared to immunization of mice with the immunogenic composition lacking the adjuvant.

15. A method of decreasing infection from human papilloma virus in an individual or increasing regression of Human Papilloma Virus (HPV)-associated cervical lesions in an HPV positive individual, comprising:
  administering an immunogenic composition comprising:
    (a) a peptide comprising SEQ ID NO: 32, a peptide comprising SEQ ID NO: 33, a peptide comprising SEQ ID NO: 34, and a peptide comprising SEQ ID NO: 35, wherein each peptide does not comprise full-length HPV E6 protein; and
    (b) an adjuvant comprising antigens from *Candida albicans*, mumps virus, or *Trichophyton*.

16. The method of claim 15 wherein the adjuvant is concentrated whole cell extract made from lyophilized cells of *Candida albicans*.

17. The method of claim 15 wherein the method comprises administering the immunogenic composition intradermally.

18. The method of claim 1 wherein the immunogenic composition comprises synthetic peptides consisting of SEQ ID NO: 32, SEQ ID NO: 33, SEQ ID NO: 34, and SEQ ID NO: 35.

19. The method of claim 15 wherein the at least one peptide is a synthetic peptide acetylated at the amino terminus, amidated at the carboxyl terminus or acetylated at the amino terminus and amidated at the carboxyl terminus.

20. The method of claim 15 wherein the peptides consist of SEQ ID NO: 32, SEQ ID NO: 33, SEQ ID NO: 34, and SEQ ID NO: 35.

* * * * *

SEQUENCE LISTING

```
<160> NUMBER OF SEQ ID NOS: 37

<210> SEQ ID NO 1
<211> LENGTH: 9
<212> TYPE: PRT
<213> ORGANISM: Artificial Sequence
<220> FEATURE:
<223> OTHER INFORMATION: E6 75-83 peptide from immunodominant epitope
      region of Human Papilloma Virus 16 E6 protein

<400> SEQUENCE: 1

Lys Phe Tyr Ser Lys Ile Ser Glu Tyr
                5

<210> SEQ ID NO 2
<211> LENGTH: 10
<212> TYPE: PRT
<213> ORGANISM: Artificial Sequence
<220> FEATURE:
<223> OTHER INFORMATION: E6 133-142 peptide from immunodominant epitope
      region of Human Papilloma Virus 16 E6 protein

<400> SEQUENCE: 2

His Asn Ile Arg Gly Arg Trp Thr Gly Arg
                5                   10

<210> SEQ ID NO 3
<211> LENGTH: 13
<212> TYPE: PRT
```

```
<213> ORGANISM: Artificial Sequence
<220> FEATURE:
<223> OTHER INFORMATION: E6 49-61 peptide from immunodominant epitope
      region of Human Papilloma Virus 16 E6 protein

<400> SEQUENCE: 3

Val Tyr Asp Phe Ala Phe Arg Asp Leu Cys Ile Val Tyr
                 5                  10

<210> SEQ ID NO 4
<211> LENGTH: 14
<212> TYPE: PRT
<213> ORGANISM: Artificial Sequence
<220> FEATURE:
<223> OTHER INFORMATION: E6 75-88 peptide from immunodominant epitope
      region of Human Papilloma Virus 16 E6 protein

<400> SEQUENCE: 4

Lys Phe Tyr Ser Lys Ile Ser Glu Tyr Arg His Tyr Cys Tyr
                 5                  10

<210> SEQ ID NO 5
<211> LENGTH: 16
<212> TYPE: PRT
<213> ORGANISM: Artificial Sequence
<220> FEATURE:
<223> OTHER INFORMATION: E6 127-142 peptide from immunodominant epitope
      region of Human Papilloma Virus 16 E6 protein

<400> SEQUENCE: 5

Asp Lys Lys Gln Arg Phe His Asn Ile Arg Gly Arg Trp Thr Gly
                 5                  10                  15

Arg

<210> SEQ ID NO 6
<211> LENGTH: 28
<212> TYPE: PRT
<213> ORGANISM: Artificial Sequence
<220> FEATURE:
<223> OTHER INFORMATION: E6 11-38 peptide from immunodominant epitope
      region of Human Papilloma Virus 16 E6 protein

<400> SEQUENCE: 6

Asp Pro Gln Glu Arg Pro Arg Lys Leu Pro Gln Leu Cys Thr Glu
                 5                  10                  15

Leu Gln Thr Thr Ile His Asp Ile Ile Leu Glu Cys Val
                20                  25

<210> SEQ ID NO 7
<211> LENGTH: 40
<212> TYPE: PRT
<213> ORGANISM: Artificial Sequence
<220> FEATURE:
<223> OTHER INFORMATION: E6 49-88 peptide from immunodominant epitope
      region of Human Papilloma Virus 16 E6 protein

<400> SEQUENCE: 7

Val Tyr Asp Phe Ala Phe Arg Asp Leu Cys Ile Val Tyr Arg Asp
                 5                  10                  15

Gly Asn Pro Tyr Ala Val Cys Asp Lys Cys Leu Lys Phe Tyr Ser
                20                  25                  30

Lys Ile Ser Glu Tyr Arg His Tyr Cys Tyr
            35                  40

<210> SEQ ID NO 8
```

```
<211> LENGTH: 9
<212> TYPE: PRT
<213> ORGANISM: Artificial Sequence
<220> FEATURE:
<223> OTHER INFORMATION: peptide sequence homologous to the E6 75-83
      epitope of Human Papilloma Virus 16 E6 protein

<400> SEQUENCE: 8

Arg Phe Leu Ser Lys Ile Ser Glu Tyr
                5

<210> SEQ ID NO 9
<211> LENGTH: 9
<212> TYPE: PRT
<213> ORGANISM: Artificial Sequence
<220> FEATURE:
<223> OTHER INFORMATION: peptide sequence homologous to the E6 75-83
      epitope of Human Papilloma Virus 16 E6 protein

<400> SEQUENCE: 9

Leu Phe Tyr Ser Lys Ile Arg Glu Tyr
                5

<210> SEQ ID NO 10
<211> LENGTH: 9
<212> TYPE: PRT
<213> ORGANISM: Artificial Sequence
<220> FEATURE:
<223> OTHER INFORMATION: peptide sequence homologous to the E6 75-83
      epitope of Human Papilloma Virus 16 E6 protein

<400> SEQUENCE: 10

Arg Phe Leu Ser Lys Ile Ser Glu Tyr
                5

<210> SEQ ID NO 11
<211> LENGTH: 9
<212> TYPE: PRT
<213> ORGANISM: Artificial Sequence
<220> FEATURE:
<223> OTHER INFORMATION: peptide sequence homologous to the E6 75-83
      epitope of Human Papilloma Virus 16 E6 protein

<400> SEQUENCE: 11

Leu Phe Tyr Ser Lys Val Arg Lys Tyr
                5

<210> SEQ ID NO 12
<211> LENGTH: 9
<212> TYPE: PRT
<213> ORGANISM: Artificial Sequence
<220> FEATURE:
<223> OTHER INFORMATION: peptide sequence homologous to the E6 75-83
      epitope of Human Papilloma Virus 16 E6 protein

<400> SEQUENCE: 12

Lys Phe Tyr Ser Lys Ile Arg Glu Tyr
                5

<210> SEQ ID NO 13
<211> LENGTH: 10
<212> TYPE: PRT
<213> ORGANISM: Artificial Sequence
<220> FEATURE:
<223> OTHER INFORMATION: peptide sequence homologous to the E6 133-142
      epitope of Human Papilloma Virus 16 E6 protein

<400> SEQUENCE: 13
```

His Asn Ile Gly Gly Arg Trp Thr Gly Arg
            5                   10

<210> SEQ ID NO 14
<211> LENGTH: 10
<212> TYPE: PRT
<213> ORGANISM: Artificial Sequence
<220> FEATURE:
<223> OTHER INFORMATION: peptide sequence homologous to the E6 133-142
      epitope of Human Papilloma Virus 16 E6 protein

<400> SEQUENCE: 14

His Asn Ile Ser Gly Arg Trp Ala Gly Arg
            5                   10

<210> SEQ ID NO 15
<211> LENGTH: 10
<212> TYPE: PRT
<213> ORGANISM: Artificial Sequence
<220> FEATURE:
<223> OTHER INFORMATION: peptide sequence homologous to the E6 133-142
      epitope of Human Papilloma Virus 16 E6 protein

<400> SEQUENCE: 15

Ala Asn Cys Trp Gln Arg Thr Arg Gln Arg
            5                   10

<210> SEQ ID NO 16
<211> LENGTH: 10
<212> TYPE: PRT
<213> ORGANISM: Artificial Sequence
<220> FEATURE:
<223> OTHER INFORMATION: peptide sequence homologous to the E6 133-142
      epitope of Human Papilloma Virus 16 E6 protein

<400> SEQUENCE: 16

His Asn Ile Met Gly Arg Trp Thr Gly Arg
            5                   10

<210> SEQ ID NO 17
<211> LENGTH: 10
<212> TYPE: PRT
<213> ORGANISM: Artificial Sequence
<220> FEATURE:
<223> OTHER INFORMATION: peptide sequence homologous to the E6 133-142
      epitope of Human Papilloma Virus 16 E6 protein

<400> SEQUENCE: 17

His Asn Ile Ser Gly Arg Trp Thr Gly Arg
            5                   10

<210> SEQ ID NO 18
<211> LENGTH: 10
<212> TYPE: PRT
<213> ORGANISM: Artificial Sequence
<220> FEATURE:
<223> OTHER INFORMATION: E6 11-19 peptide from immunodominant epitope
      region of Human Papilloma Virus 16 E6 protein

<400> SEQUENCE: 18

His Asn Ile Ser Gly Arg Trp Thr Gly Arg
            5                   10

<210> SEQ ID NO 19
<211> LENGTH: 9
<212> TYPE: PRT
<213> ORGANISM: Artificial Sequence
<220> FEATURE:

<223> OTHER INFORMATION: E6 29-37 peptide from immunodominant epitope
      region of Human Papilloma Virus 16 E6 protein

<400> SEQUENCE: 19

Thr Ile His Asp Ile Ile Leu Glu Cys
                5

<210> SEQ ID NO 20
<211> LENGTH: 10
<212> TYPE: PRT
<213> ORGANISM: Artificial Sequence
<220> FEATURE:
<223> OTHER INFORMATION: E6 29-38 peptide from immunodominant epitope
      region of Human Papilloma Virus 16 E6 protein

<400> SEQUENCE: 20

Thr Ile His Asp Ile Ile Leu Glu Cys Val
                5                   10

<210> SEQ ID NO 21
<211> LENGTH: 8
<212> TYPE: PRT
<213> ORGANISM: Artificial Sequence
<220> FEATURE:
<223> OTHER INFORMATION: E6 31-38 peptide from immunodominant epitope
      region of Human Papilloma Virus 16 E6 protein

<400> SEQUENCE: 21

His Asp Ile Ile Leu Glu Cys Val
                5

<210> SEQ ID NO 22
<211> LENGTH: 9
<212> TYPE: PRT
<213> ORGANISM: Artificial Sequence
<220> FEATURE:
<223> OTHER INFORMATION: E6 49-57 peptide from immunodominant epitope
      region of Human Papilloma Virus 16 E6 protein

<400> SEQUENCE: 22

Val Tyr Asp Phe Ala Phe Arg Asp Leu
                5

<210> SEQ ID NO 23
<211> LENGTH: 10
<212> TYPE: PRT
<213> ORGANISM: Artificial Sequence
<220> FEATURE:
<223> OTHER INFORMATION: E6 52-61 peptide from immunodominant epitope
      region of Human Papilloma Virus 16 E6 protein

<400> SEQUENCE: 23

Phe Ala Phe Arg Asp Leu Cys Ile Val Tyr
                5                   10

<210> SEQ ID NO 24
<211> LENGTH: 9
<212> TYPE: PRT
<213> ORGANISM: Artificial Sequence
<220> FEATURE:
<223> OTHER INFORMATION: E6 80-88 peptide from immunodominant epitope
      region of Human Papilloma Virus 16 E6 protein

<400> SEQUENCE: 24

Ile Ser Glu Tyr Arg His Tyr Cys Tyr
                5

```
<210> SEQ ID NO 25
<211> LENGTH: 8
<212> TYPE: PRT
<213> ORGANISM: Artificial Sequence
<220> FEATURE:
<223> OTHER INFORMATION: E7 7-15 peptide from immunodominant epitope
      region of Human Papilloma Virus 16 E7 protein

<400> SEQUENCE: 25

Thr Leu His Glu Tyr Met Leu Asp
              5

<210> SEQ ID NO 26
<211> LENGTH: 10
<212> TYPE: PRT
<213> ORGANISM: Artificial Sequence
<220> FEATURE:
<223> OTHER INFORMATION: E7 11-20 peptide from immunodominant epitope
      region of Human Papilloma Virus 16 E7 protein

<400> SEQUENCE: 26

Tyr Met Leu Asp Leu Gln Pro Glu Thr Thr
              5                  10

<210> SEQ ID NO 27
<211> LENGTH: 9
<212> TYPE: PRT
<213> ORGANISM: Artificial Sequence
<220> FEATURE:
<223> OTHER INFORMATION: E7 79-87 peptide from immunodominant epitope
      region of Human Papilloma Virus 16 E7 protein

<400> SEQUENCE: 27

Leu Glu Asp Leu Leu Met Gly Thr Leu
              5

<210> SEQ ID NO 28
<211> LENGTH: 9
<212> TYPE: PRT
<213> ORGANISM: Artificial Sequence
<220> FEATURE:
<223> OTHER INFORMATION: E7 44-52 peptide from immunodominant epitope
      region of Human Papilloma Virus 16 E7 protein

<400> SEQUENCE: 28

Gln Ala Glu Pro Asp Arg Ala His Tyr
              5

<210> SEQ ID NO 29
<211> LENGTH: 25
<212> TYPE: PRT
<213> ORGANISM: Artificial Sequence
<220> FEATURE:
<223> OTHER INFORMATION: E6 91-115 peptide from immunodominant epitope
      region of Human Papilloma Virus 16 E6 protein

<400> SEQUENCE: 29

Tyr Gly Thr Thr Leu Glu Gln Gln Tyr Asn Lys Pro Leu Cys Asp
              5                  10                  15
Leu Leu Ile Arg Cys Ile Asn Cys Gln Lys
             20                  25

<210> SEQ ID NO 30
<211> LENGTH: 25
<212> TYPE: PRT
<213> ORGANISM: Artificial Sequence
<220> FEATURE:
<223> OTHER INFORMATION: E7 46-70 peptide from immunodominant epitope
``` region of Human Papilloma Virus 16 E7 protein

<400> SEQUENCE: 30

Glu Pro Asp Arg Ala His Tyr Asn Ile Val Thr Phe Cys Cys Lys
1               5                   10                  15
Cys Asp Ser Thr Leu Arg Leu Cys Val Gln
            20                  25

<210> SEQ ID NO 31
<211> LENGTH: 25
<212> TYPE: PRT
<213> ORGANISM: Artificial Sequence
<220> FEATURE:
<223> OTHER INFORMATION: E6 46-70 peptide from immunodominant epitope
      region of Human Papilloma Virus 16 E6 protein

<400> SEQUENCE: 31

Arg Arg Glu Val Tyr Asp Phe Ala Phe Arg Asp Leu Cys Ile Val
1               5                   10                  15
Tyr Arg Asp Gly Asn Pro Tyr Ala Val Cys
            20                  25

<210> SEQ ID NO 32
<211> LENGTH: 45
<212> TYPE: PRT
<213> ORGANISM: Artificial Sequence
<220> FEATURE:
<223> OTHER INFORMATION: E6 1-45 epitope of Human Papilloma Virus 16 E6
      protein

<400> SEQUENCE: 32

Met His Gln Lys Arg Thr Ala Met Phe Gln Asp Pro Gln Glu Arg
1               5                   10                  15
Pro Arg Lys Leu Pro Gln Leu Cys Thr Glu Leu Gln Thr Thr Ile
            20                  25                  30
His Asp Ile Ile Leu Glu Cys Val Tyr Cys Lys Gln Gln Leu Leu
        35                  40                  45

<210> SEQ ID NO 33
<211> LENGTH: 35
<212> TYPE: PRT
<213> ORGANISM: Artificial Sequence
<220> FEATURE:
<223> OTHER INFORMATION: E6 46-80 epitope of Human Papilloma Virus 16
      E6 protein

<400> SEQUENCE: 33

Arg Arg Glu Val Tyr Asp Phe Ala Phe Arg Asp Leu Cys Ile Val
1               5                   10                  15
Tyr Arg Asp Gly Asn Pro Tyr Ala Val Cys Asp Lys Cys Leu Lys
            20                  25                  30
Phe Tyr Ser Lys Ile
        35

<210> SEQ ID NO 34
<211> LENGTH: 35
<212> TYPE: PRT
<213> ORGANISM: Artificial Sequence
<220> FEATURE:
<223> OTHER INFORMATION: E6 81-115 epitope of Human Papilloma Virus 16
      E6 protein

<400> SEQUENCE: 34

Ser Glu Tyr Arg His Tyr Cys Tyr Ser Leu Tyr Gly Thr Thr Leu
1               5                   10                  15

-continued

```
                5                  10                 15
Glu Gln Gln Tyr Asn Lys Pro Leu Cys Asp Leu Leu Ile Arg Cys
                    20                  25                  30

Ile Asn Cys Gln Lys
        35

<210> SEQ ID NO 35
<211> LENGTH: 43
<212> TYPE: PRT
<213> ORGANISM: Artificial Sequence
<220> FEATURE:
<223> OTHER INFORMATION: E6 116-158 epitope of Human Papilloma Virus 16
      E6 protein

<400> SEQUENCE: 35

Pro Leu Cys Pro Glu Glu Lys Gln Arg His Leu Asp Lys Lys Gln
                5                   10                  15

Arg Phe His Asn Ile Arg Gly Arg Trp Thr Gly Arg Cys Met Ser
                    20                  25                  30

Cys Cys Arg Ser Ser Arg Thr Arg Arg Glu Thr Gln Leu
            35                  40

<210> SEQ ID NO 36
<211> LENGTH: 10
<212> TYPE: PRT
<213> ORGANISM: Artificial Sequence
<220> FEATURE:
<223> OTHER INFORMATION: E6 48-57 epitope of Human Papilloma Virus 16 E6
      protein

<400> SEQUENCE: 36

Glu Val Tyr Asp Phe Ala Phe Arg Asp Leu
                5                   10

<210> SEQ ID NO 37
<211> LENGTH: 15
<212> TYPE: PRT
<213> ORGANISM: Artificial Sequence
<220> FEATURE:
<223> OTHER INFORMATION: E6 46-60 epitope of Human Papilloma Virus 16
      E6 protein

<400> SEQUENCE: 37

Arg Arg Glu Val Tyr Asp Phe Ala Phe Arg Asp Leu Cys Ile Val
                5                   10                  15
```